US007998734B2

(12) United States Patent
High et al.

(10) Patent No.: US 7,998,734 B2
(45) Date of Patent: Aug. 16, 2011

(54) METHODS AND COMPOSITIONS FOR USE IN GENE THERAPY FOR TREATMENT OF HEMOPHILIA

(75) Inventors: Katherine A. High, Merion, PA (US); Roland W. Herzog, Glenolden, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 578 days.

(21) Appl. No.: 11/932,017

(22) Filed: Oct. 31, 2007

(65) Prior Publication Data

US 2008/0213222 A1 Sep. 4, 2008

Related U.S. Application Data

(60) Continuation of application No. 09/393,844, filed on Sep. 10, 1999, now abandoned, which is a division of application No. 09/038,910, filed on Mar. 12, 1998, now Pat. No. 6,093,392.

(60) Provisional application No. 60/040,711, filed on Mar. 14, 1997.

(51) Int. Cl.
*C12N 15/00* (2006.01)
*C12N 15/86* (2006.01)

(52) U.S. Cl. ............... 435/320.1; 435/455; 435/456

(58) Field of Classification Search .......... None
See application file for complete search history.

(56) References Cited

U.S. PATENT DOCUMENTS

| 5,139,941 | A | 8/1992 | Muzyczka et al. | 435/456 |
| 5,547,932 | A | 8/1996 | Curiel et al. | 435/85 |
| 5,817,784 | A | 10/1998 | Theill et al. | 514/44 |
| 5,834,266 | A | 11/1998 | Crabtree et al. | 435/172.3 |
| 5,834,306 | A | 11/1998 | Webster et al. | 435/320.1 |
| 5,846,528 | A | 12/1998 | Podsakoff et al. | 424/93.2 |
| 5,858,351 | A | 1/1999 | Podsakoff et al. | 424/93.2 |
| 5,866,552 | A | 2/1999 | Wilson et al. | 514/44 |
| 6,342,390 | B1 | 1/2002 | Wiener et al. | 435/325 |

FOREIGN PATENT DOCUMENTS

| EP | 88 116 366 | 9/1983 |
| WO | WO 96/15777 | 5/1966 |
| WO | WO 96/18727 | 6/1996 |
| WO | WO 98/09657 | 3/1998 |

OTHER PUBLICATIONS

Kung, et al. In Vivo Expression of Therapeutic levels of Human F.I.X. using a recombinant Adeno-Associated Viral (AAV) Vector, *Blood*, 1996, 88, 273.
Kessler, et al., "Gene Delivery to Skeletal Muscle Results in Sustained Expression and Systemic Delivery of a Therapeutic Protein", *Proc. Natl. Acad. Sci.* USA, 1996, 93, 14082-14087.
Anson, et al., *Embo J.*, 1984, 3, 1053-1060.
Carter, *Curr. Opin. Biotech*, 1992, 3, 533-539.
Cheung, et al., *Proc. Natl. Acad. Sci.* USA, 1996, 93, 11068-11073.
Dai, et al., *Proc. Natl. Acad. Sci.* USA, 1995, 92, 1401-1405.
Evans, et al., *Proc. Natl. Acad. Sci.* USA, 1989, 86, 10095-10099.
Evans, et al., *Blood*, 1989, 74, 207-212.
Fisher, et al., *J. Virol*, 1996, 70, 520-532.
Fujikawa, et al., "Factor XI", *Molecular Basis of Thrombosis and Hemostasis*, High and Roberts, eds, Marcel Dekker, Inc., 1995.
Hathaway and Goodnight, "Laboratory Measurement of Hemostasis and Thrombosis", *Disorders of Hemostasis and Thrombosis: A Clinical Guide*, 1993, 21-29.
High, "Factor IX" Molecular Structure, Epitopes and Mutations Associated with Inhibitor Formation, Louis M. Aledort, eds., 1995, 79-85.
High, et al., "Factor IX" Molecular Basis of Thrombosis and Hemostasis, Marcel Dekker, Inc, eds., 1995, 215-237.
Jallat, et al., *EMBO J*, 1990, 9, 3295-3301.
Jaye, et al., *Nucl. Acids Res.*, 1983, 11, 2325-2335.
Kaplitt, et al., *Nature Genet.*, 1994, 8, 148-154.
Katayama, et al., *Proc. Natl. Acad. Sci.* USA, 1979, 76, 4990-4994.
Kay, et al., *Science*, 1993, 262, 117-119.
Kay et al., *Proc. Natl. Acas. Sci.* USA, 1994, 91, 2353-2357.
Kay, et al., *T.I.G.*, 1994, 10, 253-257.
Kotin, *Human Gene Therapy*, 1994, 5, 793-801.
Kurachi, et al., *Proc. Natl. Acad. Sci.* USA, 1982, 79, 6461-6464.
Kurachi, et al., *J Biol. Chem.*, 1995, 270, 5276-5281.
Lai, et al., "Factor XIII", *Molecular Basis of Thrombosis and Hemostasis*, High and Roberts, eds., Marcel Dekker, Inc. 1995.
McLaughlin, et al., *J. Virol.*, 1988, 62, 1963-1973.
Parker Ponder, "Gene Therapy for Blood Protein Deficiencies", *Gene Transfer in Cardiovascular Biology: Experimental Approaches and Therapeutic Implications*, 1996, Keith March, eds.
Pendurthi, et al., *Thromb Res.*, 1992, 65, 177-186.
Petersen, et al., "Factor VII", *Molecular Basis of Thrombosis and Hemostasis*, High and Roberts, eds., Marcel Dekker, Inc. 1995.
Ross, et al., *Human Gene Therapy*, 1996, 7, 1781-1790.
Samulski, et al., *J. Virol.*, 1989, 63, 3822-3828.
Sarkar, et al., *Genomics*, 1990, 6, 133-143.
Skulimowski, et al., *Method Mol. Genet.*, 1995, 7, 3-12.
Suzuki., "Protein C", *Molecular Basis of Thrombosis and Hemostasis*, High and Roberts, eds., Marcel Dekker, Inc. 1995.
Tripathy, et al., *Nature Med.*, 1996, 2, 545-550.
Tripathy, et al., *Proc. Natl. Acad. Sci.* USA, 1996, 93, 10876-10880.
Tuddenham, "Factor VIII", *Molecular Basis of Thrombosis and Hemostasis*, High and Roberts, eds., Marcel Dekker, Inc, 1995.
Walter, et al., *Proc. Natl. Acad. Sci* USA, 1996, 93, 3056-3061.
Watzke, et al., "Factor X", *Molecular Basis of Thrombosis and Hemostasis*, High and Roberts, eds., Marcel Dekker, Inc, 1995.
Wu, et al., *Gene*, 1990, 86, 275-278.
Yang, et al., *Hum, Mol. Genet.*, 1996, 5, 1703-1712.
Yoshitake, et al., *Biochemistry*, 1985, 24, 3736-3750.
Gnatenko, et al., "Generation and Characterization of Recombinant Adeno-Associated Viral (rAAV) Vectors for Factor VIII gene Therapy", *Blood*, 1996, 88(10), Part ½, 139A, Abstract 543, XP001053457.

(Continued)

*Primary Examiner* — Maria Leavitt
(74) *Attorney, Agent, or Firm* — Woodcock Washburn LLP

(57) ABSTRACT

The invention includes a composition comprising a recombinant adeno-associated viral vector comprising at least two adeno-associated virus inverted terminal repeats, a promoter/regulatory sequence, isolated DNA encoding Factor IX and accompanying 5' and 3' untranslated regions and a transcription termination.

8 Claims, 17 Drawing Sheets

OTHER PUBLICATIONS

Kessler, et al., "Gene Delivery to Skeletal Muscle Results in Sustained Expression and Systemic Delivery of a Therapeutic Protein", *Proc. Natl. Acad. Sci* USA., 1996, 93(24), 14082-14087, XP002287407.

Koerberl, et al., "Persistent Expression of Human Clotting Factor IX from Mouse Liver after Intravenous Injection of Adeno-Associated Virus Vectors", *Proc. Natl. Acad. Sci.* USA, 1997, 94(4), 1426-1431, XP002287408.

Chen, et al., "Comparison of Retroviral and Adeno-Associated Viral Vectors Designed to Express Human Clotting Factor IX", *Human Gene Therapy*, 1997, 8(2), 125-135, XP009029448.

Wiener, et al., "Stable Production in Vitro of Human Coagulation Factor IX Expressed from Adeno-Associated Virus", *Blood*, 1996, 88(10), part 1/2, 138A, Abstract 541, XP008032518.

Kotin, "Prospects for the Use of Adeno-Associated Virus as a Vector for Human Gene Therapy", 1994, 5, 793-801, XP002911111.

Fisher, et al., "Recombinant Adeno-Associated Virus for Muscle Directed Gene Therapy", Database Biosis [Online] Biosciences Information Service, 1997, Abstract, XP 002287409.

Richards, F.M., "Protein Stability: Still an Unsolved Problem", *Cell Mol. Life Sci.*, 1997, 53(10), 790-802.

Lai, et al., "Recombinant Adeno-Associated Virus Type-2-Mediated Gene Delivery in to the RPE65-/- Knockout mouse Eye Results in Lamented Rescue", *Genetic vaccines and Therapy*, 2004, 2,3, 1-15.

Miao, et al., "Nonrandom Transduction of Recombinant Adeno-Associated Virus Vectors in Mouse Hepatocytes in Vivo: Cell Cycling does not Influence Hepatocyte Transduction", *J. of Virology*, Apr. 2000, 3793, 38-3.

Wang, et al., "Construction of Human Factor IX Expression Vectors in Retroviral Frames Optimized for Muscle Cells", *Human Gene Ther.*, 1996, 7(14), 1743-1756.

Anderson., 1998, *Nature*, 392, 25.

Muzyczka., *J. Clin. Invest.*, 1994, 94, 1351.

Smith, et al., *Nat. Genet.*, 1993, 5(4), 397-402.

Miyanohara, et al., *New Biol.*, 1992, 4(3), 238-246.

Roman, et al., *Somatic Cell and Molecular Genetics.*, 1992, 18, 247-258.

Kaufman, et al., *Methods in Enzymology*, 185, 487-511, 1997.

weeks post injection

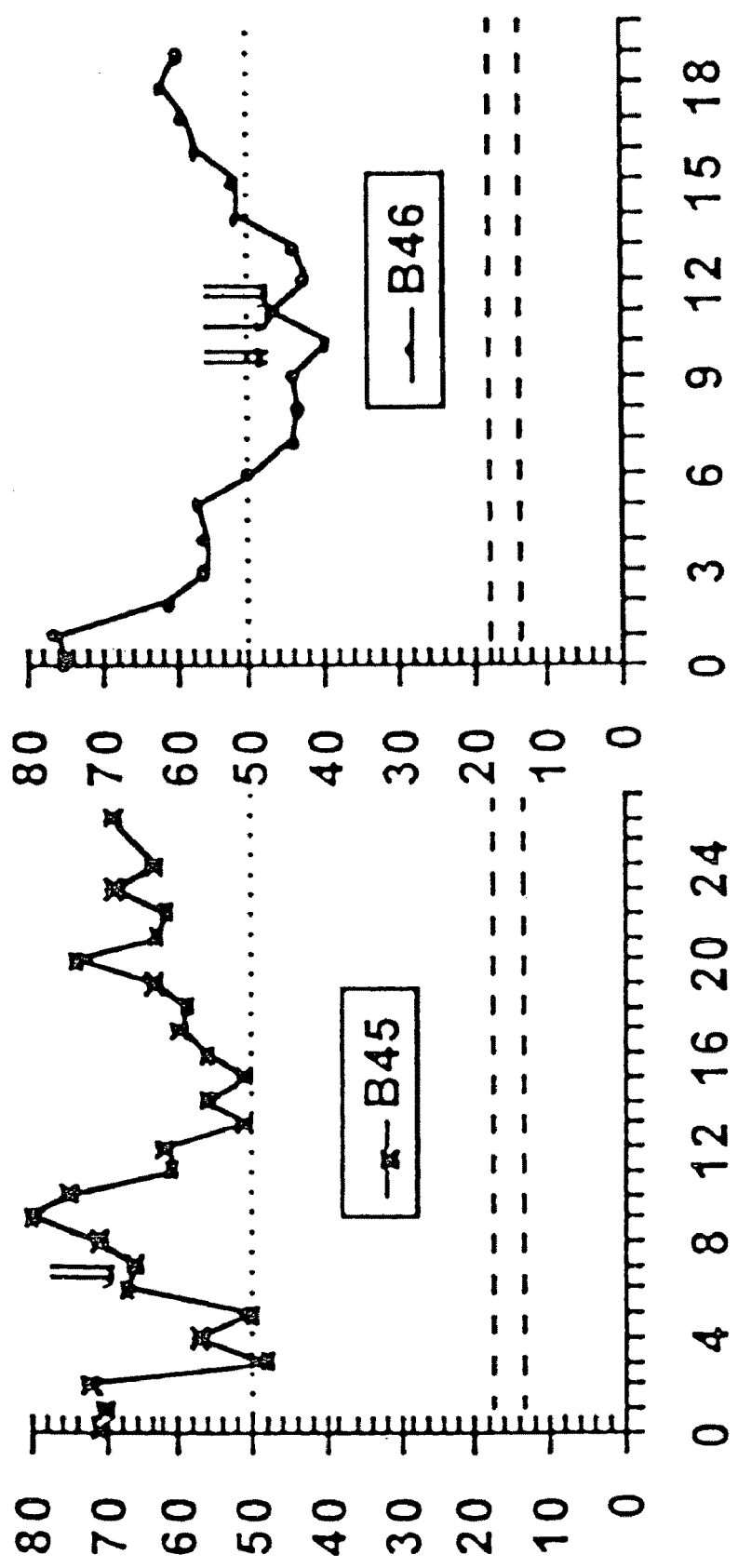

weeks post injection

```
                        SEQUENCE LISTING

<160> NUMBER OF SEQ ID NOS: 6

<210> SEQ ID NO 1
<211> LENGTH: 11
<212> TYPE: DNA
<213> ORGANISM: Artificial Sequence
<220> FEATURE:
<223> OTHER INFORMATION: Synthetic Construct

<400> SEQUENCE: 1
agatctccac c                                                        11

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
ataagctgca ataaacaagt                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
catggtaata gcgatgacta                                               20

<210> SEQ ID NO 4
<211> LENGTH: 20
<212> TYPE: DNA
<213> ORGANISM: Artificial Sequence
```

```
<220> FEATURE:
<223> OTHER INFORMATION: Synthetic Construct

<400> SEQUENCE: 4
gctctgctta tatagacctc                                            20

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5
atagcagcta caatccagct accattctgc                                 30

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
tggtatcccg tagtacagga acaaaccacc                                 30
```

METHODS AND COMPOSITIONS FOR USE IN GENE THERAPY FOR TREATMENT OF HEMOPHILIA

CROSS REFERENCE TO RELATED APPLICATIONS

This application is a continuation application of U.S. application Ser. No. 09/393,844, filed Sep. 10, 1999, which is a divisional application of U.S. Pat. No. 6,093,392, filed Mar. 12, 1998, which claims benefit of U.S. Provisional Application Ser. No. 60/040,711, filed on Mar. 14, 1997. The contents of U.S. application Ser. No. 09/393,844 and U.S. Pat. No. 6,093,392 are incorporated herein by reference.

REFERENCE TO GOVERNMENT GRANTS

Portions of the disclosure herein may have been supported in part by grants from the United States Government (National Institutes of Health Grant Nos. R01 HL53688 and P50 HL54500). The United States Government may have certain rights in this application.

FIELD OF THE INVENTION

The field of the invention is gene therapy for treatment of diseases involving a deficiency of proteins in the blood stream.

BACKGROUND OF THE INVENTION

The process of blood coagulation involves a series of proteins known as blood coagulation proteins which act in a cascade fashion to effect the formation of a blood clot. Hemophilia is a disease of humans and other mammals wherein a gene encoding a blood coagulation factor contains a mutation such that the encoded protein does not function normally in the cascade process. Specifically, the hereditary disease, hemophilia B, is characterized by a mutation in the gene encoding the blood coagulation protein, Factor IX (F.IX). F.IX is reviewed in High et al. (1995, "Factor IX" In: Molecular Basis of Thrombosis and Hemostasis, High and Roberts, eds., Marcel Dekker, Inc.).

Adenoviral vectors are well known in gene therapy and have been used to effect expression of high levels of canine factor IX in immunodeficient mice or in immunocompetent mice when the virus is administered in conjunction with immunosuppressive agents. When adenoviral vectors are administered to immunocompetent mice in the absence of immunosuppressive agents, these vectors induce a strong inflammatory and cytotoxic T lymphocyte (CTL) response (Dai et al., 1995, Proc. Natl. Acad. Sci. USA 92:1401-1405) which negates the beneficial effects of the therapy. In addition, there are reports which suggest that intramuscular injection of replication defective adenovirus provides long-term expression of a transgene, provided that the transgene encodes a self-protein (i.e., a host protein), such that a strong host immune response is avoided (Tripathy et al., 1996, Nature Med. 2:545-550; Yang et al., 1996, Hum. Mol. Genet. 5:1703-1712). Thus, while there has been significant progress in the area of gene therapy in in vivo expression of a selected transgene following direct injection of an adenoviral vector into skeletal muscle, the use of adenoviral vectors may not be the optimal method for gene therapy in light of these immunological considerations.

Retroviral vectors have also been used experimentally as a model for treatment of hemophilia B. However, levels of expression of F.IX from these vectors are reported to be too low to be of therapeutic value (Kay et al., 1993, Science 262:117-119).

Plasmid DNA which has been injected into mouse muscle has been shown to direct expression of erythropoietin (Epo) (Tripathy et al., 1996, Proc. Natl. Acad. Sci. USA 93:10876-10880), but this method of gene therapy is apparently not sufficiently efficient for the expression of a gene product such as F.IX, which is needed at relatively high levels in the circulation (compared with Epo) to achieve a therapeutic effect.

Adeno-associated virus (AAV) is an alternative vehicle to adenovirus for delivery of genes to muscle. Recombinant AAV (rAAV) does not contain sequences encoding viral proteins and has the potential to integrate into the chromosomal DNA of the host cell (Carter, 1992, Curr. Opin. Biotech. 3:533-539; Skulimowski et al., 1995, Method Mol. Genet. 7:7-12). Production and purification procedures are now available which facilitate the generation of pure rAAV which is not significantly contaminated by wild-type AAV or helper adenovirus (Skulimowski et al., 1995, supra; Fisher et al., 1996, J. Virol. 70:520-532; Samulski et al., 1989, J. Virol. 63:3822-3828). As noted herein, administration of adenovirus to mammals is accompanied by the aforementioned immunological problems.

While the efficiency of in vivo transduction with rAAV in the absence of helper virus is low for hepatocytes and airway epithelial cells (Fisher, 1996, supra), certain post-mitotic cells such as neurons (Kaplitt et al., 1994, Nature Genet. 8:148-154) and skeletal muscle fibers (Xiao et al., J. Virol. 70:8098-8108) can be effectively transduced with this vector. Stable expression of lacZ for up to 1.5 years has been reported (Xiao et al., supra). In contrast to adenoviral vectors, intramuscular injection with rAAV in immunocompetent animals does not result in a CTL response against transduced muscle fibers, nor are circulating antibodies against the intracellular lacZ gene product present.

The expression of the secreted protein, Epo, following intramuscular injection with rAAV is reported in Kessler et al. (1996, Proc. Natl. Acad. Sci. USA 93:14082-14087). However, the levels of protein expression reported were one to two orders of magnitude below that required for a therapeutic effect mediated by F.IX.

Current therapy for hemophilia involves the intravenous injection of a preparation of clotting factor concentrates whenever a bleed occurs. This treatment is cumbersome, inconvenient and very expensive. The average patient pays approximately $100,000 per year for the concentrate alone. Further, because the concentrate is only administered to the patient intermittently, patients remain at risk for life-threatening bleeds which are fatal if treatment is not timely administered.

There is a long felt and acute need for methods of delivering F.IX to mammals having hemophilia, in particular, to humans having hemophilia, such that a therapeutic effect is achieved. The present invention satisfies this need.

SUMMARY OF THE INVENTION

The invention relates to a composition comprising a recombinant adeno-associated virus vector comprising at least two adeno-associated virus inverted terminal repeats, a promoter/regulatory sequence, isolated DNA encoding Factor IX and accompanying 5' and 3' untranslated regions and a transcription termination signal.

In one aspect, the composition further comprises a portion of intron I of a Factor IX gene. Preferably, the portion of intron I of a Factor IX gene is from about 0.3 kb to about 1.7 kb in length.

In another aspect, the isolated DNA encoding Factor IX comprises a mutation which renders Factor IX encoded thereby incapable of binding to collagen IV.

In one embodiment, mutation in the mutated DNA encodes an alanine residue in place of lysine in the fifth amino acid position from the beginning of mature F.IX.

In yet another aspect, the composition further comprises a pharmaceutically acceptable carrier.

In another aspect, promoter/regulatory sequence is selected from the group consisting of the cytomegalovirus immediate early promoter/enhancer, the skeletal muscle actin promoter and the muscle creatine kinase promoter/enhancer. Additionally, the transcription termination signal is the SV40 transcription termination signal.

Also included in the invention is a kit comprising a vector comprising at least two adeno-associated virus inverted terminal repeats, a promoter/regulatory sequence, isolated DNA encoding Factor IX and accompanying 5' and 3' untranslated regions and a transcription termination signal, and instructions for using the kit.

The invention also includes a method of treating hemophilia in a mammal. The method comprises administering to a muscle tissue of the mammal a composition comprising a recombinant adeno-associated virus vector comprising at least two adeno-associated virus inverted terminal repeats, a promoter/regulatory sequence, isolated DNA encoding Factor IX and accompanying 5' and 3' untranslated regions and a transcription termination signal, and a pharmaceutically acceptable carrier.

In one aspect, the recombinant adeno-associated virus vector is administered by injecting the composition into at least two sites in the muscle tissue.

In a preferred embodiment, the recombinant adeno-associated virus vector is administered by injecting the composition into at least six sites in the muscle tissue.

In another aspect, the recombinant adeno-virus vector is administered at a dose of between about $1 \times 10^8$ to about $5 \times 10^{16}$ viral vector genomes per mammal.

In a preferred embodiment, the mammal is a human and the Factor IX is human Factor IX.

In yet another aspect, the promoter/regulatory sequence is selected from the group consisting of the cytomegalovirus immediate early promoter/enhancer, the skeletal muscle actin promoter and the muscle creatine kinase promoter/enhancer.

In another aspect, the composition further comprises a portion of intron I of a Factor IX gene. Preferably, the portion of intron I of a Factor IX gene is from about 0.3 kb to about 1.7 kb.

In yet another aspect, the isolated DNA encoding Factor IX comprises a mutation which renders Factor IX encoded thereby incapable of binding to collagen IV.

In a preferred embodiment, the mutation in the mutated DNA encodes an alanine residue in place of lysine in the fifth amino acid position from the beginning of mature F.IX. In addition, preferably, the mammal is a human.

BRIEF DESCRIPTION OF THE DRAWINGS

FIG. 1A represents C57BL/6 mice following IM injection of $2 \times 10^{11}$ viral vector genomes/animal (n=4). FIG. 1B represents Rag 1 mice following IM injection of $2 \times 10^{11}$ viral vector genomes/animal (n=4). Mouse o-o died 5 weeks post-injection following traumatic phlebotomy. FIG. 1C represents Rag 1 mice following IM injection of $1 \times 10^{10}$ viral vector genomes/animal (n=4).

FIG. 4A represents uninjected muscle. FIGS. 4B, 4C and 4D represent muscle stained at three months post-injection with AAV-hF.IX. $3.3 \times 10^{10}$ viral vector genomes were inoculated per injection site. The magnification is 200×.

FIG. 5A represents fluorescence of FITC (green) showing the presence of hF.IX in muscle fibers and interstitial spaces. FIG. 5B represents fluorescence of rhodamine (red) showing collagen IV in the extracellular matrix of muscle fibers. FIG. 5C represents simultaneous excitation of both fluorescence tags. Note the presence of a yellow signal in the interstitial spaces indicating that hF.IX and collagen IV occupy the same space in the muscle tissue. The magnification is 400×.

FIG. 6A is a diagram depicting head-to-tail tandem repeats of two AAV-hF.IX vector genomes. AAV inverted terminal repeat (ITR) sequences, CMV promoter/enhancer (CMV), human F.IX cDNA including the coding sequence, and 228-bp of the 3'-untranslated region, a 1.4 kb portion of intron I, simian virus 40 polyadenylation signal (SV40), and the junction site of the two genomes (J) are indicated on the figure. A 1.2 kb EcoRV-EcoRI fragment from intron I and a 0.7 kb BglII fragment obtained from the CMV promoter were chosen as probes for Southern blot hybridization. The relative positions of binding sites for primers 005 (forward primer), 013, and 017 (reverse primers) are also shown. FIG. 6B is an image of a Southern blot hybridization analysis of genomic DNA isolated from the muscle of a Rag 1 mouse six weeks post-injection with AAV-hF.IX. A radioactively labeled EcoRV-EcoRI fragment from intron I of hF.IX served as a probe. Lane 1 represents pAAV-FIX plasmid DNA. Lanes 2 and 3 represent DNA isolated from muscle injected with AAV-hF.IX. Lanes 4 and 5 represent DNA isolated from an uninjected animal. Lanes 1, 2 and 4 represent DNA digested with EcoRV. Lanes 3 and 5 represent undigested DNA. 15 μg of genomic DNA was added per lane in lanes 2-5. DNA was separated on a 1% agarose gel prior to transfer onto a nylon membrane (Schleicher and Schuell). Marginal size markers indicate 1 kb DNA ladder fragments. FIG. 6C is an image of Southern blot hybridization of junction fragments of head-to-tail concatamers of AAV-hF.IX amplified by PCR. PCR products amplified from genomic DNA using primer pair 005-013 (odd numbered lanes) or primer pair 005-017 (even numbered lanes) are shown. Lanes 1 and 2 represent an uninjected animal. Lanes 3-6 represent C57BL/6 mice injected IM with AAV-hF.IX. Lanes 7-10 represent Rag 1 mice injected IM with AAV-hF.IX. PCR products were obtained from DNA obtained from tibialis anterior (lanes 3, 4, 7 and 8) or quadriceps (lanes 5, 6, 9 and 10) muscle DNA. Lanes 11 and 12 represent PCR products obtained from DNA obtained from the cell line, 10-3.AV 5, which contains at least two monomer copies of integrated AAV-lacZ arranged head-to-tail. PCR products were separated on a 2% agarose gel before blotting onto a nylon membrane. A 0.7 kb BglII fragment obtained from the CMV promoter served as a probe. Genomic muscle DNA was isolated six to eight weeks post-injection.

FIGS. 9A and 9B are a series of graphs depicting clotting time by activated partial thromboplastin time (aPTT) of plasma samples obtained from dogs B45 and B46, respectively. Normal dogs: 13-18 seconds (broken lines). Untreated hemophilia B dogs: 50-80 seconds (dotted lines). Vertical arrows indicate treatment with normal plasma for bleeding.

FIG. 11A shows uninjected muscle. FIGS. 11B, 11C, and 11D show, at week 7, tibialis anterior muscle obtained from one site of injection of $5 \times 10^{10}$ AAV-cF.IX.

DETAILED DESCRIPTION OF ILLUSTRATIVE EMBODIMENTS

Figure 1A:
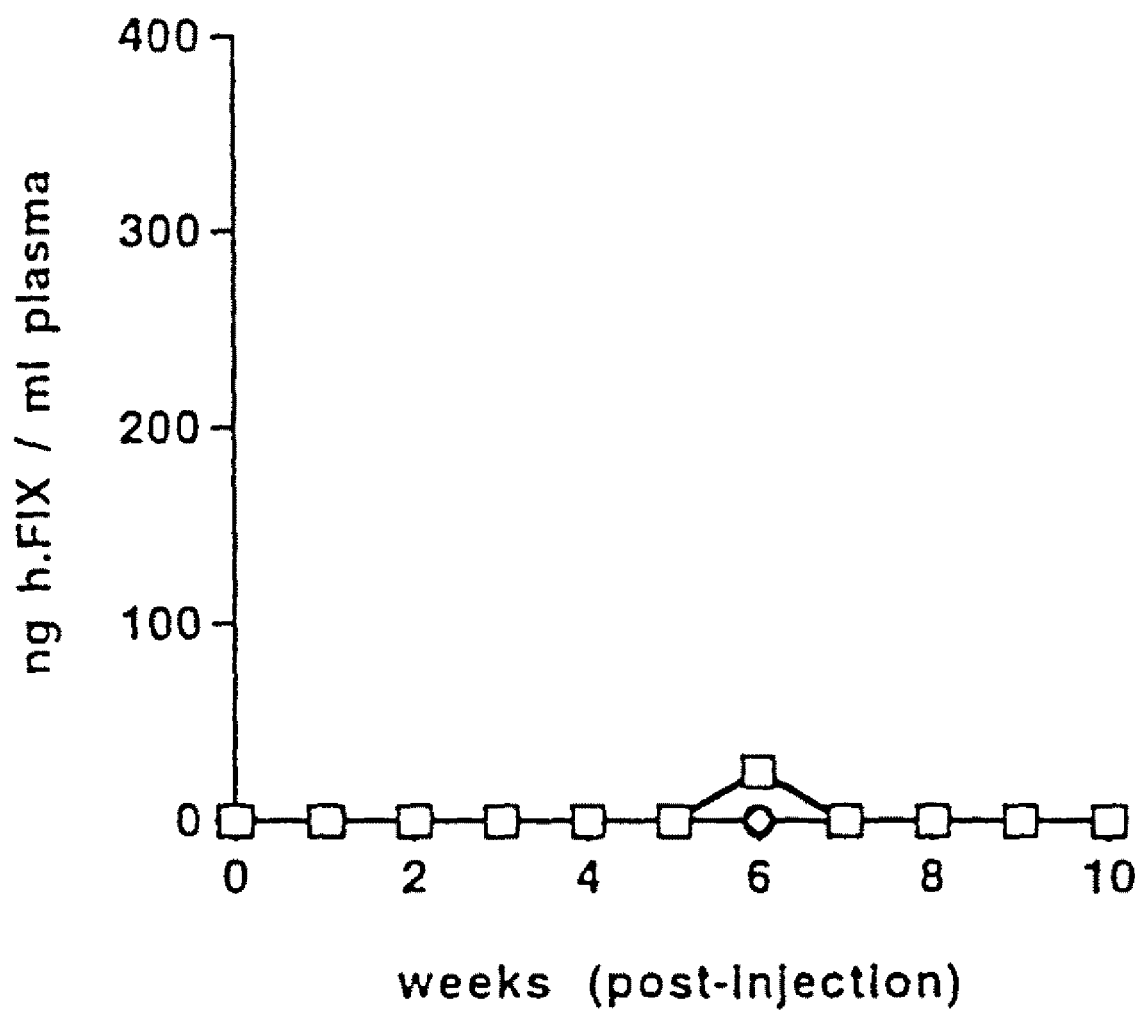
FIGS. 1A-1C are a series of graphs depicting an analysis of the concentration of human F.IX (hF.IX) in plasma in experimental mice as a function of time following intramuscular (IM) injection of the mice with AAV-hF.IX. Each line represents an individual animal.

The invention is based on the discovery that delivery of hF.IX to the muscle tissue of a mammal using an rAAV vector as a gene delivery vehicle results in long term expression of hF.IX at therapeutic levels in the muscle tissue. The expressed protein persists in the plasma of the mammal for long periods of time and therefore is of tremendous therapeutic benefit to a mammal having hemophilia B.

The invention is not limited solely to the delivery of F.IX for treatment of hemophilia B. Rather, the invention should be construed to include AAV vectors encoding other blood coagulation factors, which factors may be delivered, using the methods of the present invention, to the cells of a mammal having hemophilia for treatment of hemophilia. Thus, the invention should be construed to include: delivery of Factor VIII to a mammal for treatment of hemophilia A (Tuddenham, 1995, "Factor VIII" In: Molecular Basis of Thrombosis and Hemostasis, High and Roberts, eds., Marcel Dekker, Inc.); delivery of Factor VII for treatment of Factor VII deficiency (Petersen et al., 1995, "Factor VII" In: Molecular Basis of Thrombosis and Hemostasis, High and Roberts, eds., Marcel Dekker, Inc.); delivery of Factor X for treatment of Factor X deficiency (Watzke et al., "Factor X" 1995, In: Molecular Basis of Thrombosis and Hemostasis, High and Roberts, eds., Marcel Dekker, Inc.); delivery of Factor XI for treatment of Factor XI deficiency (Fujikawa et al., 1995, "Factor XI" In: Molecular Basis of Thrombosis and Hemostasis, High and Roberts, eds., Marcel Dekker, Inc.); delivery of Factor XIII for treatment of Factor XIII deficiency (Lai et al., 1995, "Factor XIII" In: Molecular Basis of Thrombosis and Hemostasis, High and Roberts, eds., Marcel Dekker, Inc.); and, delivery of Protein C for treatment of Protein C deficiency (Suzuki, 1995, "Protein C" In: Molecular Basis of Thrombosis and Hemostasis, High and Roberts, eds., Marcel Dekker, Inc.).

Delivery of each of the above-recited proteins to the cells of a mammal is accomplished by first generating an AAV vector comprising DNA encoding the desired protein and then administering the vector to the mammal. Thus, the invention should be construed to include AAV vectors comprising DNA encoding any one of Factor IX, Factor VIII, Factor X, Factor VII, Factor XI, Factor XIII or Protein C. Once armed with the present invention, the generation of AAV vectors comprising DNA encoding these proteins will be apparent to the skilled artisan.

Moreover, the invention should not be construed to be limited solely to an rAAV vector comprising an isolated DNA encoding a blood coagulation protein. Rather, the invention should be construed to include rAAV vectors comprising DNA encoding other proteins, which DNA is preferably administered to the muscle tissue of a mammal. Thus, the invention should be construed to include DNA encoding gene products which are useful for the treatment of other disease states in a mammal. Such DNA and associated disease states include, but are not limited to: DNA encoding glucose-6-phosphatase, associated with glycogen storage deficiency type 1A; DNA encoding phosphoenolpyruvate-carboxykinase, associated with Pepck deficiency; DNA encoding galactose-1 phosphate uridyl transferase, associated with galactosemia; DNA encoding phenylalanine hydroxylase, associated with phenylketonuria; DNA encoding branched chain α-ketoacid dehydrogenase, associated with Maple syrup urine disease; DNA encoding fumarylacetoacetate hydrolase, associated with tyrosinemia type 1; DNA encoding methylmalonyl-CoA mutase, associated with methylmalonic acidemia; DNA encoding medium chain acyl CoA dehydrogenase, associated with medium chain acetyl CoA deficiency; DNA encoding omithine transcarbamylase, associated with omithine transcarbamylase deficiency; DNA encoding argininosuccinic acid synthetase, associated with citrullinemia; DNA encoding low density lipoprotein receptor protein, associated with familial hypercholesterolemia; DNA encoding UDP-glucouronosyltransferase, associated with Crigler-Najjar disease; DNA encoding adenosine deaminase, associated with severe combined immunodeficiency disease; DNA encoding hypoxanthine guanine phosphoribosyl transferase, associated with Gout and Lesch-Nyan syndrome; DNA encoding biotinidase, associated with biotinidase deficiency; DNA encoding β-glucocerebrosidase, associated with Gaucher disease; DNA encoding β-glucuronidase, associated with Sly syndrome; DNA encoding peroxisome membrane protein 70 kDa, associated with Zellweger syndrome; DNA encoding porphobilinogen deaminase, associated with acute intermittent porphyria; DNA encoding $\alpha_1$ antitrypsin for treatment of α-1 antitrypsin deficiency (emphysema); DNA encoding erythropoietin for treatment of anemia due to thalassemia or to renal failure; and, DNA encoding insulin for treatment of diabetes. Such DNAs and their associated diseases are reviewed in Kay et al. (1994, T.I.G. 10:253-257) and in Parker Ponder (1996, "Gene Therapy for Blood Protein Deficiencies" In: Gene Transfer in Cardiovascular Biology Experimental Approaches and Therapeutic Implications, Eds. Keith March).

For the purpose of clarity and for the purpose of satisfying the best mode requirement, the discussion which follows exemplifies Factor IX as the preferred protein to be delivered to the muscle tissue of a mammal.

The invention is also based on the discovery that injection of the hF.IX-encoding rAAV vector of the invention into multiple sites in the muscle tissue of a mammal results in high level, long term expression of hF.IX in the mammal, thereby providing a therapeutic benefit to the mammal.

The invention is further based on the additional discovery that hF.IX binds to collagen IV in the interstitial spaces in mammalian muscle tissue. The delivery of mutant forms of hF.IX to the muscle tissue of a mammal via the rAAV vector of the invention, which mutant forms do not bind collagen IV, also serves to provide a therapeutic benefit to a mammal having hemophilia.

The invention includes an rAAV vector comprising an isolated DNA encoding F.IX, or a biologically active fragment thereof, for use in treatment of hemophilia.

The invention also includes a method of treating a mammal, preferably, a human, having hemophilia B. The method comprises administering to the muscle tissue of the mammal the rAAV vector of the invention.

The rAAV vector of the invention comprises several essential DNA elements. These DNA elements include at least two copies of an AAV ITR sequence, a promoter/enhancer element, a transcription termination signal, any necessary 5' or 3' untranslated regions which flank DNA encoding F.IX or a biologically active fragment thereof. The rAAV vector of the invention also includes a portion of intron I. Also, optionally, the rAAV vector of the invention comprises DNA encoding an F.IX which contains a mutation such that binding of the mutated F.IX to collagen is substantially reduced or eliminated entirely. These elements are now described in detail.

The vector may comprise a promoter/regulatory sequence which comprises a promiscuous promoter which is capable of driving expression of a heterologous gene to high levels in many different cell types. Such promoters include, but are not limited to the cytomegalovirus (CMV) immediate early promoter/enhancer sequences, the Rous sarcoma virus promoter/enhancer sequences and the like. Preferably, the promoter/regulatory sequence in the rAAV vector of the invention is the CMV immediate early promoter/enhancer. However, the promoter sequence used to drive expression of the heterologous gene may also be an inducible promoter, for example, but not limited to, a steroid inducible promoter, or may be a tissue specific promoter, such as, but not limited to, the skeletal α-actin promoter which is muscle tissue specific and the muscle creatine kinase promoter/enhancer, and the like.

As used herein, the term "promoter/regulatory sequence" means a DNA sequence which is required for expression of a gene operably linked to the promoter/regulator sequence. In some instances, this sequence may be the core promoter sequence and in other instances, this sequence may also include an enhancer sequence and other regulatory elements which are required for expression of the gene in an inducible/repressible or tissue-specific manner.

By describing two DNAs as being "operably linked" as used herein, is meant that a single-stranded or double-stranded DNA comprises each of the two DNAs and that the two DNAs are arranged within the DNA in such a manner that at least one of the DNA sequences is able to exert a physiological effect by which it is characterized upon the other.

The rAAV vector of the invention also comprises a transcription termination signal. While any transcription termination signal may be included in the vector of the invention, preferably, the transcription termination signal is the SV40 transcription termination signal.

The vector also includes a portion of intron I. When referring to the sequence of hF.IX, intron I is a fragment of DNA which includes the 5' end of the intron up to the first PvuII site (at nucleotide number 1098) and the 3' end of the intron beginning at a PvuII site at nucleotide number 5882 and extending to the junction with exon 2 (Yoshitake et al., 1985, Biochemistry 24:3736-3750; Kurachi et al., 1995, J. Biol. Chem. 270:5276-5281; Jallat et al., 1990, EMBO J. 9:3295-3301).

Inclusion of an intron element in a plasmid or viral vector encoding F.IX may enhance expression of F.IX by 2- to 10-fold compared with expression of F.IX on a plasmid or viral template in the absence of the intron element (Kurachi et al., 1995, supra). AAV vectors typically accept inserts of DNA having a defined size range which is generally about 4 kb to about 4.8 kb, and the coding region of the F.IX gene comprises about 1.5 kb. Thus, it is necessary to include additional DNA in the insert fragment in order to achieve the required length of DNA which is acceptable for the AAV vector. The F.IX intron I fragment fulfills this requirement while also enhancing expression of F.IX positioned in the background of an AAV vector genome. Thus, it will be appreciated that the invention is not limited to the inclusion of intron I sequences in the rAAV vector of the invention, but should be construed to include other intron or other DNA fragment sequences in place of portions of intron I.

By the term "a portion of intron I" as used herein, is meant region of intron I having a nucleotide length of from about 0.3 kb to about 1.7 kb, which region enhances expression of F.IX by at least about 1.5-fold on a plasmid or viral vector template when compared with expression of F.IX in the absence of a portion of intron I. Preferably, the portion of intron I useful in the present invention is about 1.4 kb in length.

The rAAV vector of the invention also comprises 5' and 3' untranslated regions of DNA which flank the hF.IX DNA sequence. In the rAAV-hF.IX vector exemplified in the experimental examples section, the 5' untranslated region flanking the hF.IX sequences is as follows: At the 5' end of the F.IX sequences, the CMV promoter enhancer sequence continues, at its 3' end, until a KpnI site having the sequence GGTACC. A short polylinker sequence follows directly downstream of this region, having the sequence AGATCTC-CACC [SEQ ID NO: 1], which is itself followed directly downstream by the hF.IX sequence beginning at amino acid number −46, the codon for which is an ATG following the numbering system recited in Yoshitake et al. (1985, supra).

In the rAAV-hF.IX vector exemplified in the experimental details section, the 3' untranslated region flanking the hF.IX sequences is as follows: At the end of the translation stop signal, the first 228 nucleotides of the 3' untranslated sequence of hF.IX are present which are spliced to the SV40 poly A signal sequences.

It will be appreciated that other 5' and 3' untranslated regions of DNA may be used in place of those recited in the case of hF.IX, particularly when DNA encoding proteins other than hF.IX is used in the rAAV vector of the invention.

The preferred rAAV vector of the invention also comprises isolated DNA encoding F.IX, or a biologically active fragment of F.IX. While the DNA encoding F.IX is preferably hF.IX, the invention should be construed to include all mammalian F.IX sequences which are either known or unknown. Examples of F.IX sequences are recited in the following articles: Yoshitake et al., 1985, supra; Kurachi et al., 1995, supra; Jallat et al., 1990, supra; Kurachi et al., 1982, Proc. Natl. Acad. Sci. USA 79:6461-6464; Jaye et al., 1983, Nucl. Acids Res. 11:2325-2335; Anson et al., 1984, EMBO J. 3: 1053-1060; Wu et al., 1990, Gene 86:275-278; Evans et al., 1989, Blood 74:207-212; Pendurthi et al., 1992, Thromb. Res. 65:177-186; Sakar et al., 1990, Genomics 1990, 6:133-143; and, Katayama et al., 1979, Proc. Natl. Acad. Sci. USA 76:4990-4994. Thus, the invention should be construed to include F.IX genes from mammals other than humans, which F.IX functions in a substantially similar manner to the hF.IX described herein. Preferably, the nucleotide sequence comprising the gene encoding F.IX is about 50% homologous, more preferably about 70% homologous, even more preferably about 80% homologous and most preferably about 90% homologous to the gene encoding hF.IX described herein and whose sequence is provided in Yoshitake et al. (1985, supra).

The use of the term "DNA encoding" should be construed to include the DNA sequence which encodes the desired protein and any necessary 5' or 3' untranslated regions accompanying the actual coding sequence.

Further, the invention should be construed to include naturally occurring variants or recombinantly derived mutants of wild type hF.IX DNA sequences, which variants or mutants render the protein encoded thereby either as therapeutically effective as full-length hF.IX, or even more therapeutically effective than full-length hF.IX in the gene therapy methods of the invention.

For example, as will be apparent from the experiments described herein, collagen IV serves to trap hF.IX which is introduced into the muscle tissue of a mammal via an rAAV vector. Some of the hF.IX so introduced is therefore not available for participation in blood coagulation because it is retained in the interstitial spaces in the muscle tissue by collagen IV. It is possible to introduce a mutation into the sequence of hF.IX DNA such that the protein encoded thereby does not bind collagen IV. Such mutants are useful in the gene therapy methods of the invention for the treatment of hemophilia in that they encode a form of hF.IX which is not trapped in the interstitial spaces of the muscle tissue. Preferably, a mutant hF.IX gene which encodes a hF.IX protein comprising the amino acid alanine in place of lysine in the fifth amino acid position from the beginning of the mature protein, is useful in the rAAV vector of the invention to reduce or eliminate binding of hF.IX to collagen IV.

The invention should also be construed to include DNA encoding variants of hF.IX which retain hF.IX biological activity. Such variants, i.e., analogs of proteins or polypeptides of hF.IX, include proteins or polypeptides which have been or may be modified using recombinant DNA technology such that the protein or polypeptide possesses additional properties which enhance its suitability for use in the methods described herein, for example, but not limited to, variants conferring enhanced stability on the protein in plasma and enhanced specific activity of the protein. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Preferably, the amino acid sequence of an hF.IX analog is about 70% homologous, more preferably about 80% homologous, even more preferably about 90% homologous, more preferably, about 95% homologous, and most preferably, at least about 99% homologous to the amino acid sequence of hF.IX described in Yoshitake et al., 1985, (supra).

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology.

Any number of procedures may be used for the generation of mutant or variant forms of F.IX. For example, generation of mutant forms of hF.IX which do not bind collagen IV may be accomplished by introducing deletion, substitution or insertion mutations into an F.IX gene residing on a plasmid template using ordinary recombinant DNA methodology described in any molecular biology manual, for example, described in Sambrook et al. (1989, Molecular Cloning: A Laboratory Manual, Cold Spring Harbor, N.Y.). Mutant F.IX so generated is expressed and the resulting protein is assessed for its ability to bind collagen IV in a collagen IV binding assay such as that described, for example, in Cheung et al.

(1996, Proc. Natl. Acad. Sci. USA 93:11068-11073). Mutant proteins which do not bind collagen IV are then tested for F.IX biological activity as defined herein. DNA encoding a mutated F.IX protein which does not bind collagen IV but retains F.IX biological activity, is suitable for use in the rAAV vector of the invention.

Procedures for the introduction of amino acid changes in a protein or polypeptide by altering the DNA sequence encoding the polypeptide are well known in the art and are also described in Sambrook et al. (1989, supra).

An "isolated nucleic acid", as used herein, refers to a nucleic acid sequence, segment, or fragment which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

By "biologically active F.IX" as used herein, is meant an F.IX protein which is capable of mediating the coagulation of blood in a blood coagulation assay. Blood coagulation assays are well known in the art and are described, for example, in Walter et al. (1996. supra) and in Hathaway and Goodnight (1993, Laboratory Measurement of Hemostasis and Thrombosis, In: Disorders of Hemostasis and Thrombosis: A Clinical Guide, pp. 21-29).

By "therapeutic effect" as used herein as it relates to F.IX, is meant coagulation of blood in the mammal following a bleed.

The invention is not limited to the specific rAAV vector exemplified in the experimental examples; rather, the invention should be construed to include any suitable AAV vector, including, but not limited to, vectors based on AAV-1, AAV-3, AAV-4 and AAV-6, and the like.

Also included in the invention is a method of treating a mammal having hemophilia in an amount effective to provide a therapeutic effect of mediating coagulation of blood in a blood coagulation assay. The method comprises administering to the mammal an rAAV vector comprising F.IX. Preferably, the mammal is a human and the rAAV vector comprises hF.IX which optionally comprises a mutation such that amino acid number five (numbered from the beginning of the mature protein) is an alanine instead of a lysine.

According to the invention, it has been discovered that there are several methods of treating a mammal having hemophilia. In one method of the invention, a preparation of rAAV vector comprising F.IX is injected into the muscle tissue of an animal at a single site per dose and in another method of the invention, a preparation of rAAV is injected into the muscle tissue of the animal either simultaneously, or over the course of several hours, at multiple muscle tissue sites. In the latter instance, when the method comprises simultaneous multiple injection of viral vector genomes, it is envisaged that a multiple delivery injection device may be used such that different areas of muscle tissue receive the rAAV vector simultaneously.

Typically, the number of viral vector genomes/mammal which are administered in a single injection ranges from about $1\times10^8$ to about $5\times10^{16}$. Preferably, the number of viral vector genomes/mammal which are administered in a single injection is from about $1\times10^{10}$ to about $1\times10^{15}$; more preferably, the number of viral vector genomes/mammal which are administered in a single injection is from about $5\times10^{11}$ to about $5\times10^{15}$; and, most preferably, the number of viral vector genomes which are administered to the mammal in a single injection is from about $5\times10^{13}$ to about $5\times10^{14}$.

When the method of the invention comprises multiple site simultaneous injections, or several multiple site injections comprising injections into different muscle sites over a period of several hours (for example, from about less than one hour to about two or three hours) the total number of viral vector genomes administered is identical to that recited in the single site injection method.

For administration of the rAAV vector of the invention in a single site injection, a suspension of virus is injected directly into the muscle.

For multiple site injection, a needle is inserted into the muscle tissue of the mammal. The vector is injected essentially continuously along the needle track so that a series of intramuscular sites are injected with each injection, each site therefore being at a position further into the muscle tissue than the previous site. Each injection will target from about 5 to about 30 sites along the needle track and patients will receive about 50 injections in all. The procedure is therefore akin to an acupuncture procedure which is preferably carried out under anesthesia.

Multiple site injection of rAAV may also be accomplished using a multiple injection device such as that commonly used for the detection of tuberculosis infection.

For administration to the mammal, the rAAV vector comprising F.IX is suspended in a pharmaceutically acceptable carrier, for example, HEPES buffered saline at a pH of about 7.8. Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The rAAV vector of the invention may also be provided in the form of a kit, the kit comprising, for example, a freeze-dried preparation of vector in a dried salts formulation, sterile water for suspension of the vector/salts composition and instructions for suspension of the vector and administration of the same to the mammal.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Stable Gene Transfer and Expression of Human Blood Coagulation Factor IX after Intramuscular Injection of Recombinant Adeno-Associated Virus The experiments presented in this example may be summarized as follows. To determine whether intramuscular injection of a recombinant AAV (rAAV) vector expressing human F.IX could direct expression of therapeutic levels of human F.IX the following experiments were performed. High titer ($10^{12}$-$10^{13}$ vector genomes/ml) of rAAV expressing hF.IX was prepared, purified and injected into the hind limb muscles of C57BL/6 mice and Rag 1 mice. In the immunocompetent C57B/6 mice, immunofluorescent staining of muscle harvested three months after injection demonstrated the presence of hF.IX protein, and PCR analysis of muscle DNA was positive for AAV DNA, but no hF.IX was detected in mouse plasma. Further, it was observed that these mice developed circulating antibodies to hF.IX. In follow-up experiments in Rag 1 mice, which have a mutation in the recombinase activating gene and thus lack functional B and T cells, similar results were seen upon DNA analysis of muscle, but these mice also demonstrated therapeutic levels (200-350 ng/ml) of hF.IX in the plasma. The time course of hF.IX expression demonstrates that levels gradually increase over a period of several weeks before reaching a plateau that is stable at about 6 months after initial injection. In other experiments, colocalization of hF.IX and collagen IV in interstitial spaces between muscle fibers was observed. Collagen IV has been identified as an hF.IX binding protein. Thus, this finding explains the unusual pattern of immunofluorescence staining for hF.IX. These experiments demonstrate that rAAV can be used to direct stable expression of therapeutic levels of hF.IX after intramuscular injection and is a feasible strategy for treatment of patients having hemophilia B.

The Materials and Methods used in the experiments presented in this example are now described.

Production and Purification of rAAV. Recombinant AAV was generated by cotransfection of a F.IX cis plasmid (pAAV-FIX) and the trans-acting plasmid pAAV/Ad (Skulimowski et al., 1995, supra) into human embryonic kidney (293) cells infected with an E1-deleted adenovirus as described by Fisher et al. (1996, supra). pAAV-FIX was derived from psub201 (Skulimowski et al., 1995, supra) and contains the CMV promoter/enhancer, the human F.IX coding sequence including 1.4 kb fragment of intron 1 (Kurachi et al., 1995, supra), and the SV40 polyadenylation signal, flanked by AAV ITR sequences. The AAV rep and cap gene functions were supplied in trans by pAAV/Ad. E1-deleted adenovirus contains a lacZ or alkaline phosphatase reporter gene to facilitate the identification of any potential contamination of rAAV stocks with helper virus. Cells were lysed 48 hours after transfection by sonication, and the released viral particles were purified by four rounds of CsCl density gradient centrifugation as described by Fisher et al. (1996, supra).

AAV-hF.IX particles had a density of 1.37-1.40 g/ml. The titer of the purified AAV-hF.IX was determined by slot blot hybridization using a probe specific to either the CMV promoter or intron I sequences. Controls comprise standards of pAAV-hF.IX plasmid DNA of known concentration. The ability of AAV-hF.IX to transduce cells in vitro was confirmed by transducing growing HeLa cells and measuring the concentration of hF.IX in the culture supernatant 36 hours post-infection with an ELISA specific for hF.IX (Walter et al., 1996, supra). AAV-hF.IX (1012-1013 genomes/ml) was stored at −79° C. in HEPES-buffered saline, pH 7.8, including 5% glycerol.

Purified AAV-hF.IX routinely lacked detectable amounts of contaminating adenovirus when analyzed by transduction of 293 cells followed by staining for alkaline phosphatase or β-galactosidase as described by Fisher et al. (1996, supra). Wild-type AAV was detected at <1 infectious unit per $10^9$ genomes of AAV-hF.IX.

The assay for wild-type AAV was as follows: 293 cells grown on chamber slides were co-infected with adenovirus and with aliquots of purified AAV-hF.IX. The cells were fixed for immunofluorescence staining at 24 hours post-infection. A mouse monoclonal antibody directed against AAV capsid proteins (American Research Products, Belmont, Mass.) served as a primary antibody, and anti-mouse IgG (DAKO Corporation, Carpinteria, Calif.) in a dilution of 1:40, served as the secondary antibody.

Animal Experiments. Mouse strains selected for intramuscular injection with rAAV were C57BL/6 (Charles River Laboratories, Wilmington, Mass.) and B6, 129 and Rag 1 (Jackson Laboratories, Bar Harbor, Me.). Female mice (4-6 weeks old) were anesthetized with an intraperitoneal injection of ketamine (70 mg/kg) and xylazine (10 mg/kg), and a 1 cm longitudinal incision was made in the lower extremity. AAV-hF.IX ($2\times10^{11}$ or $1\times10^{10}$ viral vector genomes/animal in HEPES-Buffered-Saline, pH 7.8) was injected into the tibialis anterior (25 µl) and the quadriceps muscle (50 µl) of each leg using a Hamilton syringe. Incisions were closed with 4-0 Vicryl suture. Blood samples were collected at seven-day intervals from the retro-orbital plexus in microhematocrit capillary tubes and plasma was assayed for hF.IX by ELISA. For immunofluorescence staining and DNA analysis, animals were sacrificed at selected time points and injected and non-injected muscle tissue was excised. Tissue was placed in O.C.T. embedding compound (Miles Corporation, Elkart, Ind.), snap frozen in liquid nitrogen-cooled isopentane for seven seconds, and immediately transferred to liquid nitrogen.

Assays for hF.IX Human F.IX antigen in mouse plasma was assessed by ELISA as described by Walter et al. (1996, supra). This ELISA did not cross-react with mouse F.IX. All samples were assessed in duplicate. Protein extracts obtained from injected mouse muscle were prepared by maceration of muscle in PBS containing leupeptin (0.5 mg/ml) followed by sonication. Cell debris was removed by microcentrifugation, and 1:10 dilutions of the protein extracts were assayed for hF.IX in the ELISA. Extracts obtained from AAV-lacZ injected muscle were used as negative controls. Protein concentrations were determined in a BIORAD protein assay (Bio-Rad, Hercules, Calif.).

Immunofluorescence Staining of Tissue Sections. Cryo-sections of muscle tissue (6 µg) were fixed for 15 minutes in 3% paraformaldehyde in PBS, pH 7.4, rinsed in PBS for 5 minutes, incubated in methanol for 10 minutes, washed three times in PBS, and then blocked in PBS/3% BSA for 1 hour.

Tissue sections were incubated overnight in the presence of an affinity purified goat anti-human F.IX antibody (Affinity Biologicals, Hamilton, Ontario, Canada) that was diluted 1:1000 in PBS/1% BSA. After three washes of 10 minutes each in PBS/1% BSA, the secondary antibody was applied for 90 minutes. This preparation of antibody comprised FITC-conjugated rabbit anti-goat IgG (DAKO Corporation, Carpinteria, Calif.), diluted 1:200 in PBS/1% BSA. After three additional washes in PBS/1% BSA, sections were rinsed in distilled water, air-dried and mounted with Fluoromount G mounting media (Fisher Scientific). All incubation steps were conducted at room temperature, except for incubation with the primary antibody which was conducted at 4° C. The same protocol was applied when sections were stained with rabbit anti-human collagen IV as primary antibody (Chemicon, Temecula, Calif.) in a 1:500 dilution and FITC-conjugated anti-rabbit IgG as secondary antibody.

For colocalization studies, a goat anti-hF.IX antibody conjugated to FITC (Affinity Biologicals) was applied simultaneously with the anti-collagen IV antibody. Rhodamine-conjugated anti-rabbit IgG (Chemicon) was used to detect collagen IV-antibody complexes. Fluorescence microscopy was performed with a Nikon FXA microscope.

Tests for Circulating Anti-hF.IX Antibody. Plasma samples of C57BL/6 mice which were injected IM with AAV-hF.IX were tested for the presence of antibodies against hF.IX using an ELISA. Microtiter plates were coated with hF.IX (1 μg/ml in 0.1 M NaHCO$_3$, pH 9.2). Dilute plasma samples (1:16) were applied in duplicate, and antibodies reactive with hF.IX were detected using horseradish peroxidase-conjugated anti-mouse IgG (Zymed, San Francisco, Calif.) at a dilution of 1:2000. Buffer conditions were as described (Walter et al., 1996, supra). Levels of anti-hF.IX antibody were estimated by comparison of the absorbance values of monoclonal mouse anti-hF.IX (Boehringer Mannheim) diluted to a final concentration of 1 μg/ml.

The presence of anti-hF.IX antibody was also assessed by Western blot analysis. These were performed as described by Dai et al. (1995, supra), except that a horseradish peroxidase conjugated goat anti-mouse IgG antibody (Boehringer Mannheim) was used as secondary antibody, thereby facilitating detection of hF.IX-antibody complexes with enhanced chemiluminescence (ECL) reagent (Amersham, Mass.). Samples of mouse plasma were diluted 1:500.

DNA Analyses. Genomic DNA was isolated from injected muscle tissue as described in Sambrook et al. (1989, supra). PCR reactions were performed in order to amplify head-to-tail junctions of rAAV tandem repeats. The forward primer 005 (5'-ATAAGCTGCAATAAACAAGT-3' [SEQ ID NO:2]) anneals to the SV40 polyadenylation signal (bp position 8014-8033), and reverse primers 013 (5'-CATGGTAATAGC-GATGACTA-3' [SEQ ID NO:3]) and 017 (5'-GCTCTGCT-TATATAGACCTC-3' [SEQ ID NO:4]) anneal to the CMV promoter (bp position 4625-4606 and 4828-4809). PCR reactions were performed using 100 ng genomic DNA in a total reaction volume of 100 μl including 1.5 mM MgCl$_2$, and 0.5 μM of primer pair 005/013 or 005/017. Following an initial denaturation step (94° C. for four minutes), 35 cycles of the following profile were carried out: denaturation at 94° C. for 1 minute, annealing at 52° C. for 1 minute, extension at 72° C. for 90 seconds (10 minutes during the final cycle). PCR products were cloned for DNA sequence analysis using the T/A cloning kit (Invitrogen, San Diego, Calif.). Southern blot hybridizations were performed using $^{32}$P-dCTP random primed labeled probes specific for the CMV promoter (for hybridization to PCR fragments) or for intron I of hF.IX as present in AAV-hF.IX (for hybridization to genomic mouse DNA).

The Results of the experiments presented in this example are now described.

Expression of hF.IX in Immunocompetent Mice. The recombinant AAV vector which was chosen for the in vivo experiments contains the human F.IX cDNA, including a portion of intron I, under the transcriptional control of the CMV immediate early gene promoter/enhancer and the SV40 transcription termination signal. This expression cassette is flanked by AAV ITR sequences and completely lacks AAV protein coding sequences.

Figure 2:
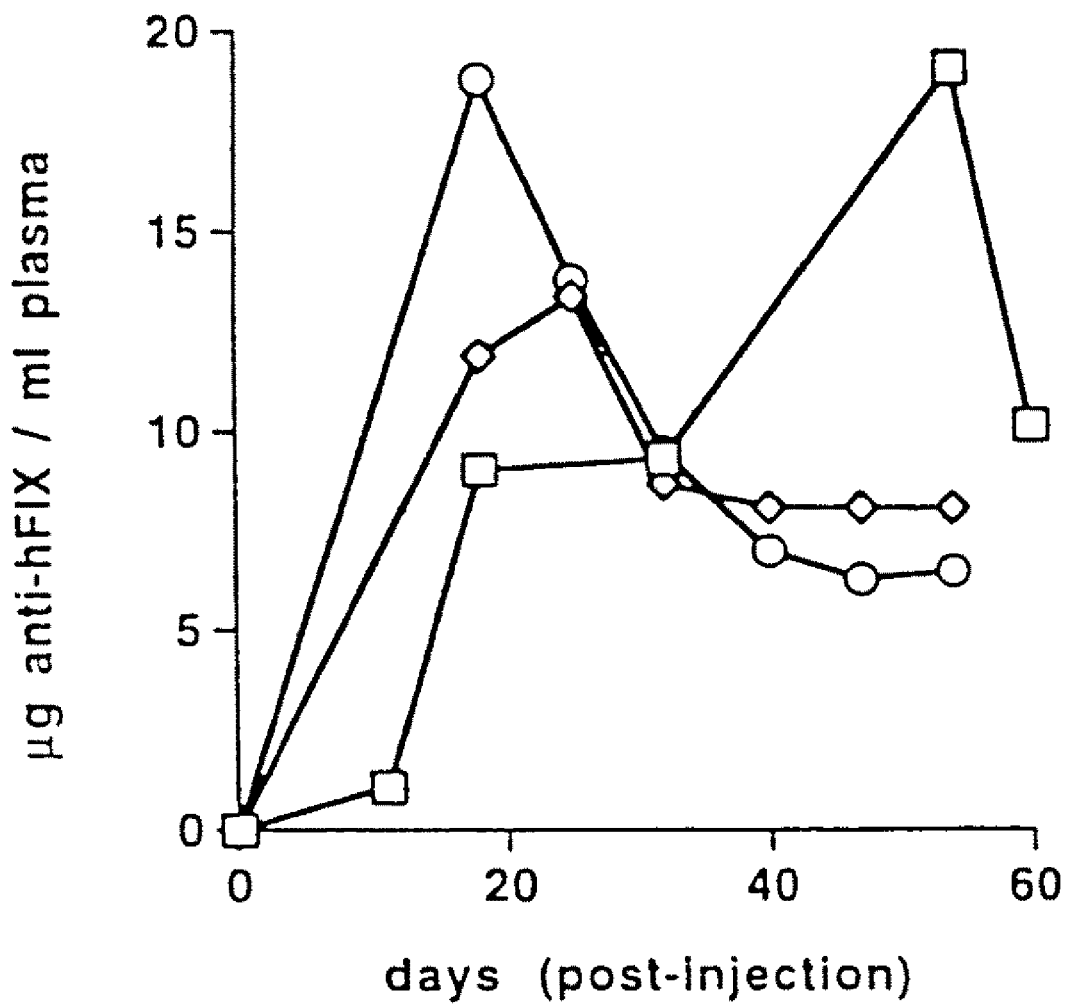
FIG. 2 is a graph depicting a time course study of the amount of circulating (plasma) anti-hF.IX antibody in C57BL/6 mice following IM injection of $2 \times 10^{11}$ AAV-hF.IX viral vector genomes/animal (n=3). The levels of antibody were measured in an ELISA assay using mouse monoclonal anti-hF.IX (Boehringer Mannheim) as a standard. Each line represents an individual animal.
Figure 3:
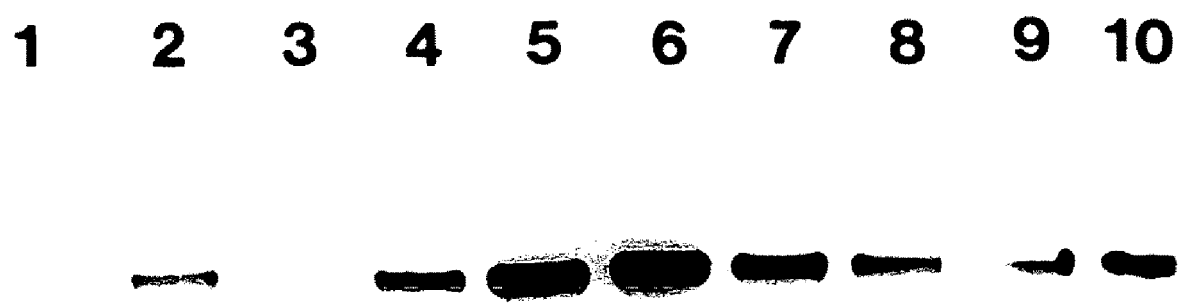
FIG. 3 is an image of a Western blot demonstrating the presence of antibodies specific for hF.IX in the plasma of C57BL/6 mice following IM injection of various viral vectors. Lane 1 represents an animal injected IM with AAV-lacZ, with serum drawn on day 18 post-injection. Lane 2 represents an animal injected IM with recombinant adenovirus-hF.IX (Walter et al., 1996, Proc. Natl. Acad. Sci. USA 93:3056-3061), with serum drawn on day 20 post-injection. Lanes 3-10 represent animals injected IM with AAV-hF.IX. Lanes 3-7 represent the same animal analyzed at days 11, 18, 32, 54, and 60 post-injection. Lanes 8-10 represent different animals analyzed at day 18 post-injection.

Following intramuscular injection of AAV-hF.IX into immunocompetent C57BL/6 mice, hF.IX was detected either transiently or not at all in the plasma of injected animals (FIG. 1A). When the same plasma samples were tested for antibodies specific for hF.IX, a strong antibody response was observed in all injected animals starting at day 11 post-injection (FIGS. 2 and 3). High levels of circulating antibody persisted for the duration of the experiment.

Figure 4:
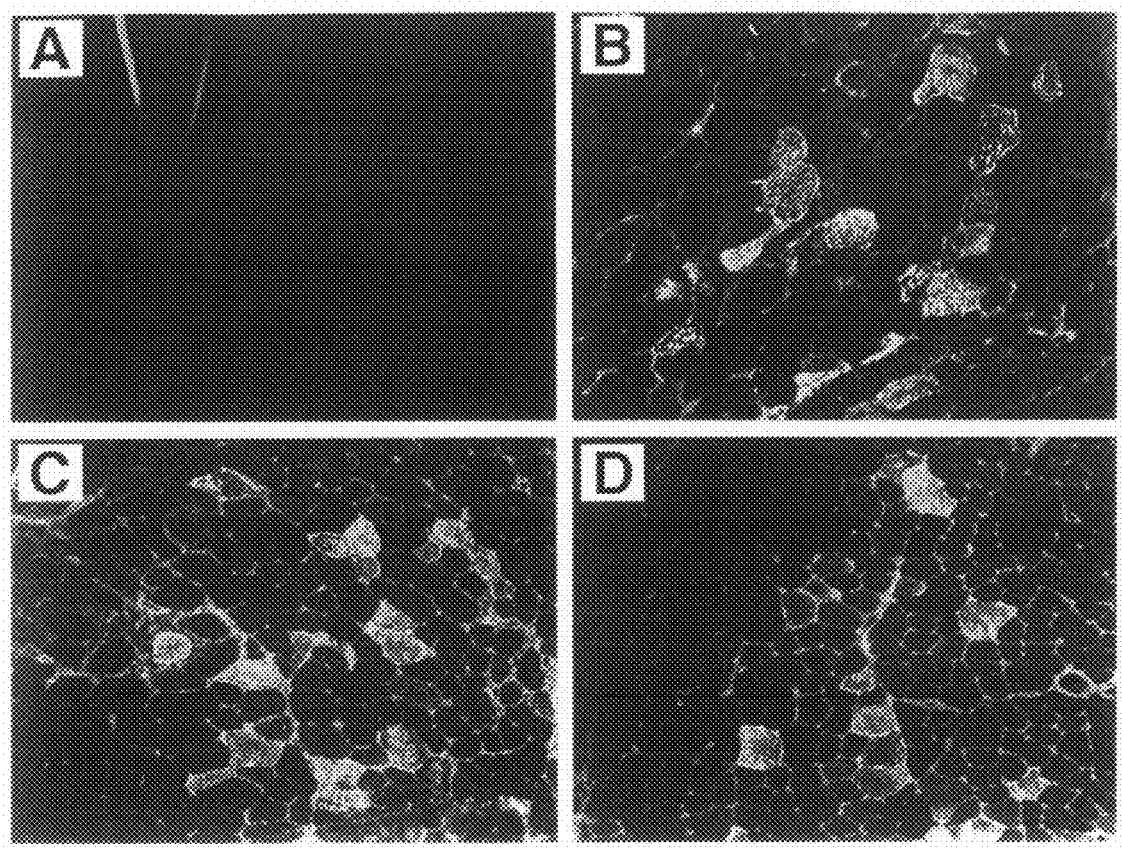
FIGS. 4A-4D are a series of images depicting immunofluorescence staining (with antibody to hF.IX) of the tibialis anterior muscle of C57BL/6 mice.

Protein extracts from injected muscles (tibialis anterior and quadriceps) from animals sacrificed at one month post-injection, revealed the presence of 1.8-2.1 ng hF.IX/mg of tissue (40-50 ng hF.IX/mg protein). This finding, i.e., the presence of hF.IX in muscle tissues as demonstrated by ELISA on protein extracts, was confirmed by immunofluorescence studies on tissue sections. FIG. 4, Panels B-D, depicts expression of human F.IX in the muscle fibers of C57BL/6 mice at three months post-injection. Note that hF.IX is present not only in the muscle fibers themselves, but is also present in the interstitial spaces between the fibers where it appears to accumulate.

Figure 5:
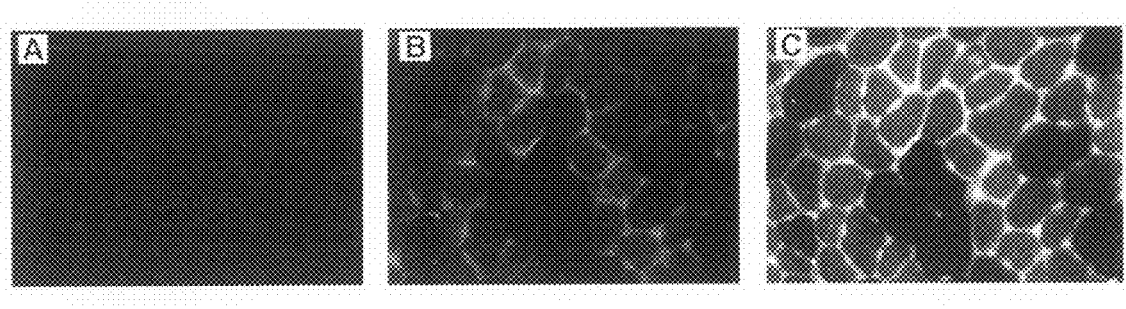
FIGS. 5A-5C are a series of images depicting immunofluorescence staining of muscle sections of the tibialis anterior muscle of C57BL/6 mice injected with AAV-hF.IX. The analysis was performed at three months following injection. Muscle sections were stained simultaneously with FITC-conjugated antibody specific for hF.IX and a rhodamine-conjugated antibody complex directed against collagen IV.

The above-described interstitial staining pattern of hF.IX in muscle tissue was identical to that seen in the same tissue using a polyclonal antibody specific for human collagen IV (FIG. 5, Panel B). Co-localization of the antibody staining of hF.IX and collagen IV was confirmed in a simultaneous staining experiment using two different fluorescence labels (FIG. 5, Panel C). It has been reported that collagen IV binds to hF.IX in vitro (Cheung et al., 1996, supra). Factor IX was not detected in uninjected muscle (FIG. 4, Panel A), nor was it detected in muscle injected with AAV-lacZ.

Inflammation or extensive tissue damage, as described for skeletal muscle injected with recombinant adenovirus, was not observed in any of the tissue sections discussed above nor in sections analyzed by hematoxylin-eosin staining.

Expression of hF.IX in Immunodeficient Mice. AAV-hF.IX was also delivered to the muscle tissue of Rag 1 mice using the procedures described above for the C57BL/6 mice. These mice are homozygous for a mutation in the recombinase activating gene 1. Rag 1 mice are therefore functionally equivalent to severe combined immunodeficiency (SCID) mice and do not produce mature B or T cells.

Figure 1B:
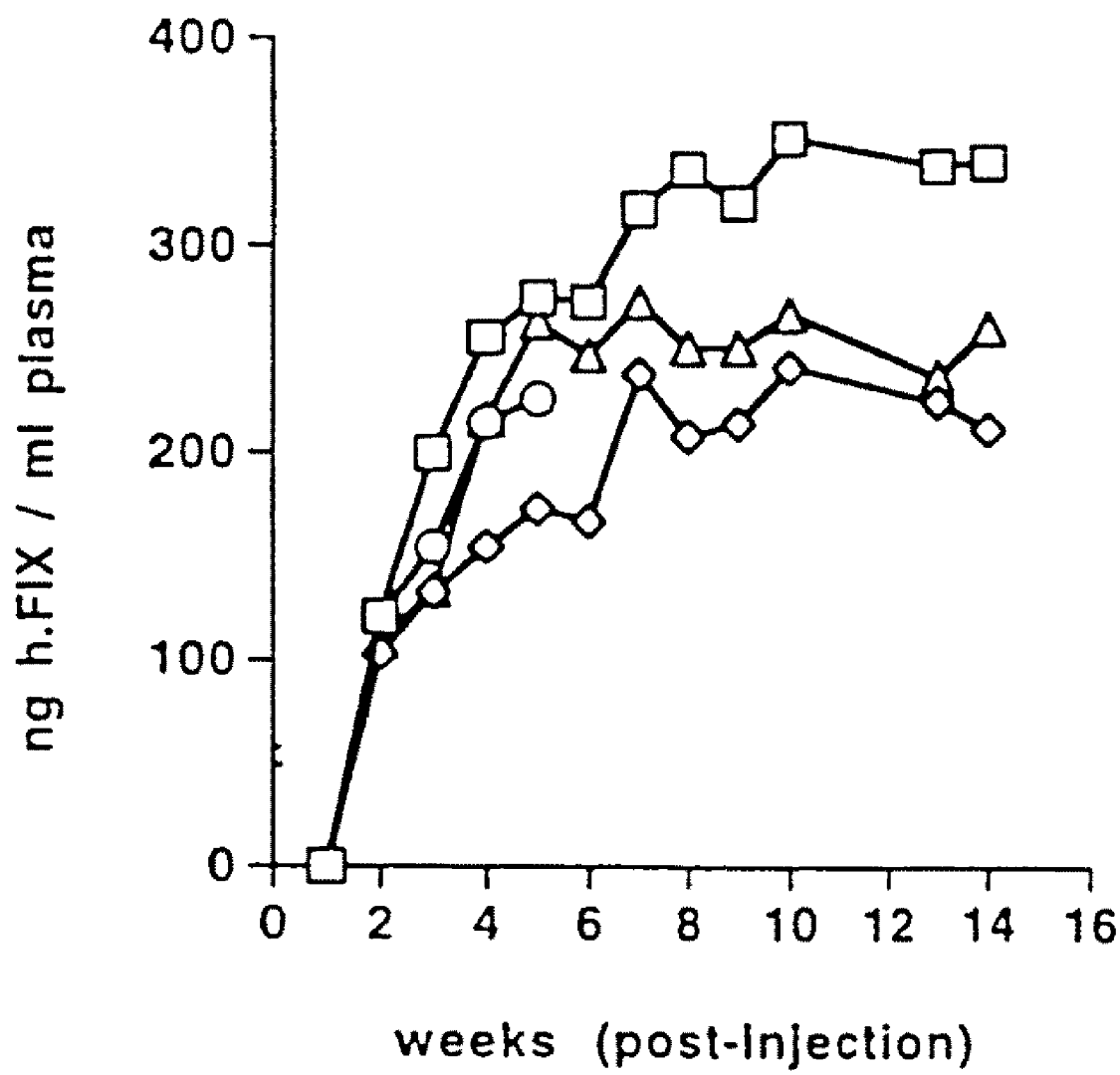
Figure 1C:
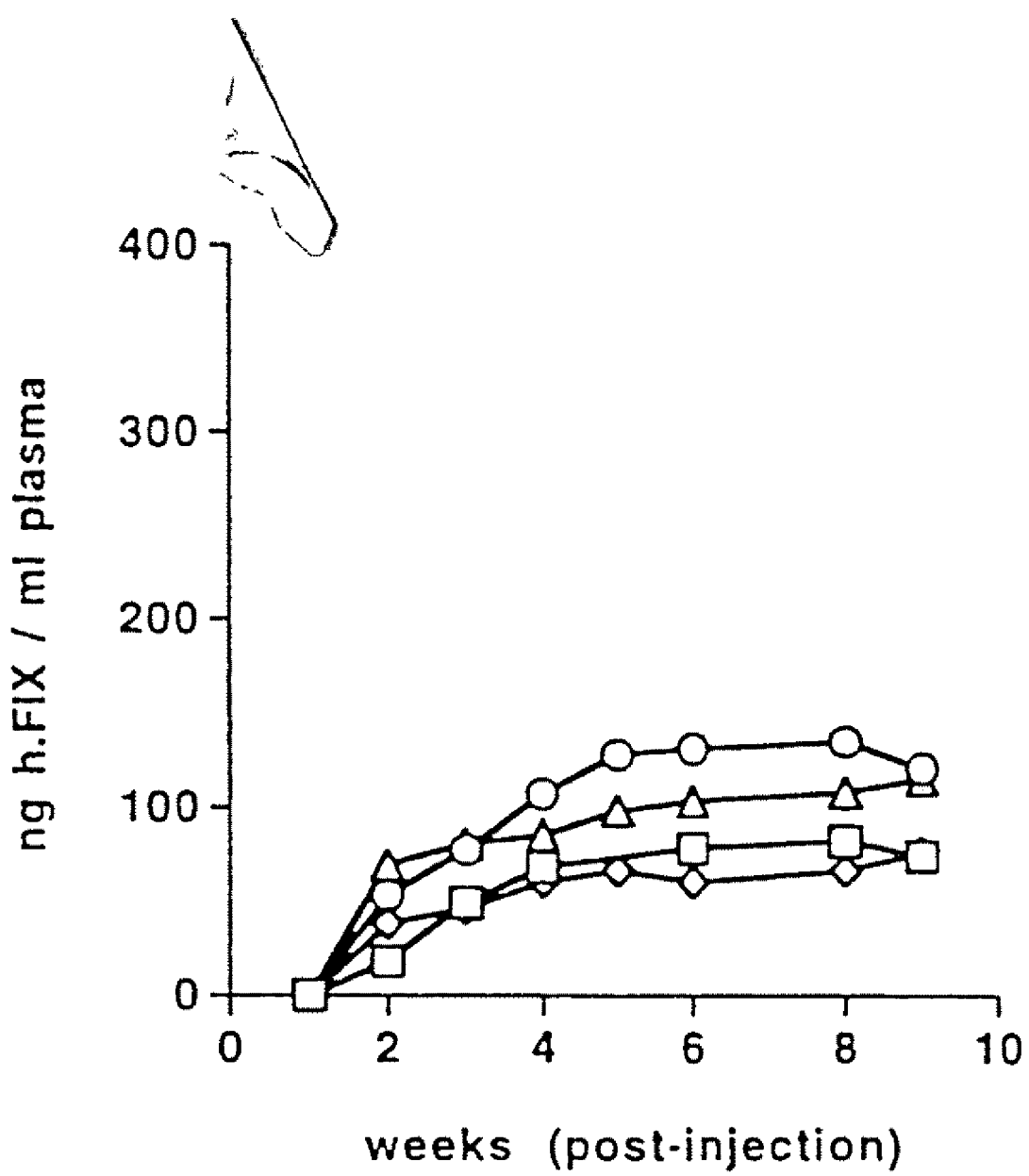

A dose of $2\times10^{11}$ viral vector genomes per Rag 1 mouse resulted in stable expression of hF.IX in mouse plasma (FIG. 1B). Human F.IX was first detectable by ELISA in the second week after the injection and rose gradually thereafter. Plasma levels reached a plateau five to seven weeks post-injection at a dose of 200 to 350 ng hF.IX/ml of mouse plasma. This level was maintained for the duration of the experiment which was extended to four months post-injection. When a total of $1\times10^{10}$ viral vector genomes were injected, expression of hF.IX was observed to be three- to four-fold lower than that observed following injection of $2\times10^{11}$ genomes; however, even when the lower dose was used, therapeutic levels (>100 ng/ml) were achieved in some animals (FIG. 1C). These results establish the fact that it is possible to administer lower doses of AAV-hF.IX to an animal and achieve a therapeutic effect. In addition, the results suggest that any given injection site becomes saturated with virus at a given threshold dose of virus; injection of an amount of virus above the threshold level does not effect a proportionate increase in the amount of circulating hF.IX in the plasma. Therefore, to increase the amount of circulating hF.IX in the plasma, multiple doses of smaller amounts of virus injected into different muscle sites are preferred.

Figure 6A:
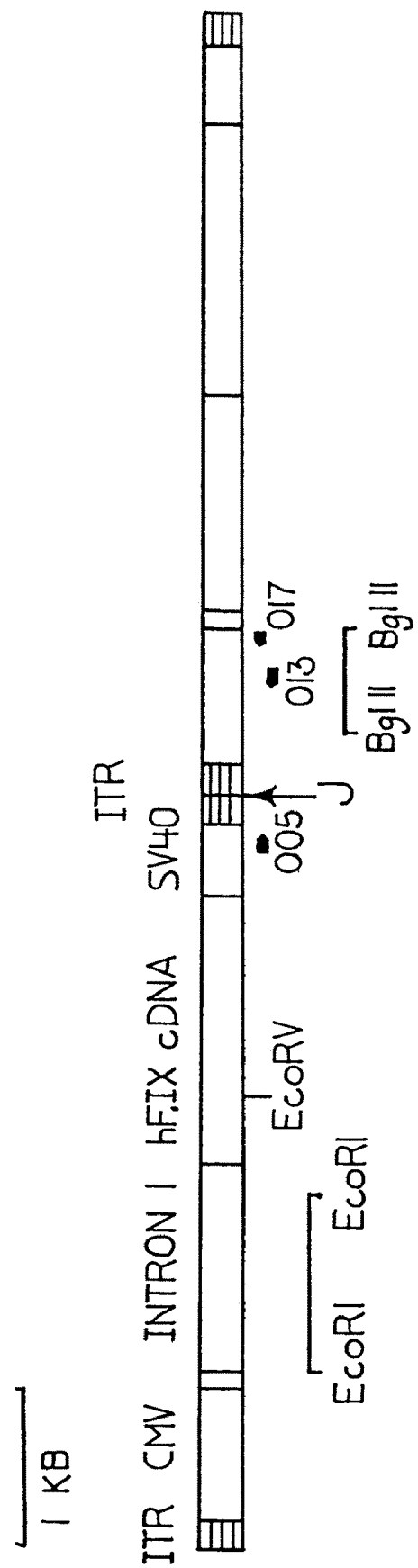
FIGS. 6A-6C are an analysis of DNA isolated from muscle injected with AAV-hF.IX.
Figure 6B:
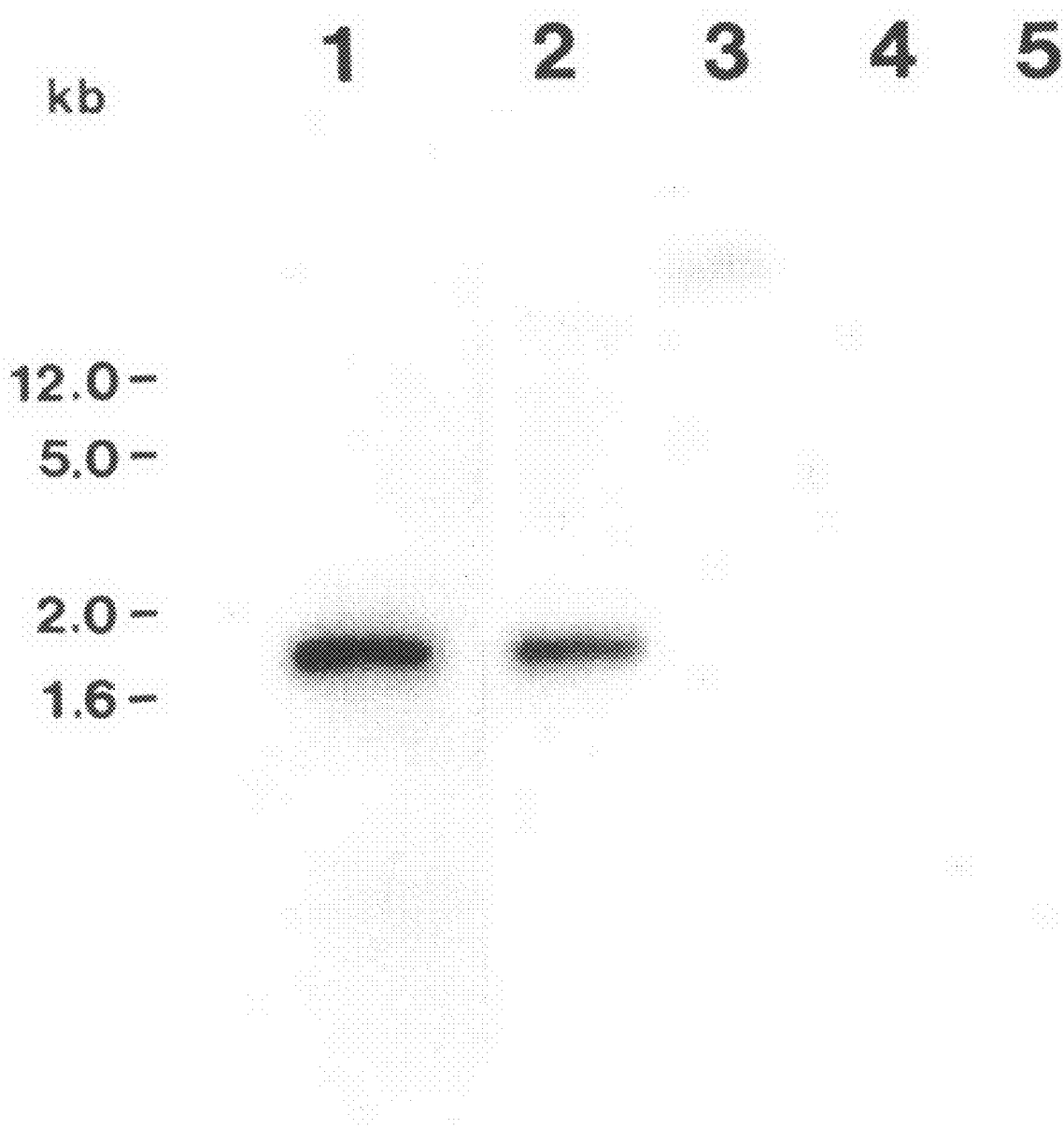

Analysis of DNA Introduced into Skeletal Muscle. Genomic DNA obtained from injected muscle tissue was isolated at six to eight weeks post-injection. The presence of the introduced vector DNA in the tissue was demonstrated by digestion of the DNA with EcoRV, which releases a 1.8 kb fragment from the vector construct including the entire 1.4 kb intron I sequence. A probe specific to intron I hybridized to this fragment (FIG. 6B, lanes 2, 3) and did not cross-hybridize to mouse DNA obtained from an uninjected animal (lanes 4, 5). Undigested DNA (FIG. 6B, lane 3) exhibited a hybridization signal in the high molecular weight DNA. Furthermore, PCR primers designed to amplify junction sequences of head-to-tail concatamers of recombinant AAV present in transduced cells (FIG. 4A) successfully amplified those sequences in muscle DNA isolated from AAV-hF.IX transduced tissue (tibialis anterior and quadriceps of immunodeficient and immunocompetent animals).

Figure 6C:
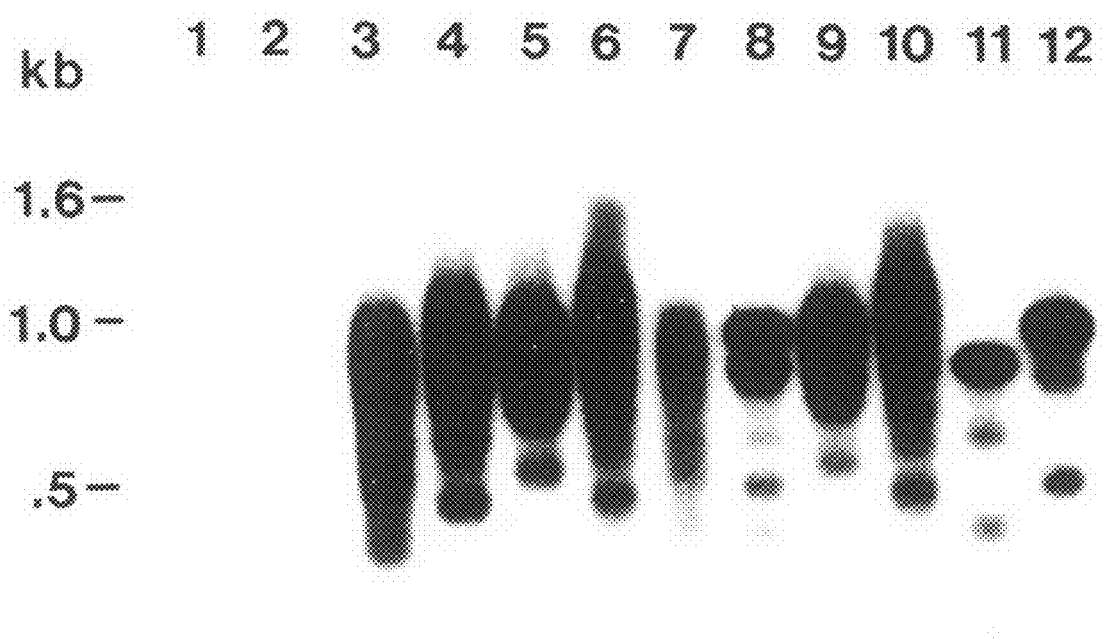

The PCR products were visualized by Southern blot hybridization using a probe specific for the CMV promoter/enhancer sequence (FIG. 6C, lanes 3-10). Primer pair 005-013 amplified fragments that were 1.0 kb and smaller; primer pair 005-017 amplified fragments that were 1.2 kb and smaller. As expected, these PCR reactions did not generate distinct bands of the sizes noted above, but rather a series of amplification products were generated having a maximum size. This result was predictable due to imprecise joining of AAV genomes present in these tandem repeats (McLaughlin et al., 1988, J. Virol. 62:1963-1973). This imprecise joining results from variable deletions of ITR sequences at the junction sites as confirmed by DNA sequencing of cloned PCR products.

The data presented herein have several implications for development of gene therapy protocols for patients with hemophilia B. First, the levels of hF.IX expression obtained in the experiments described herein are adequate to achieve a therapeutic effect in humans and are limited merely by the quantity of rAAV which can be produced. Second, it is clear from these data that multiple intramuscular injection sites are preferable to single site injections. Since muscle tissue is abundant, this does not present an obstacle for treatment of patients with hemophilia using AAV vectors.

The time course of expression of hF.IX documented herein is quite different from that observed when adenoviral vectors expressing hF.IX are used. In the latter instance, therapeutic levels of hF.IX are achieved almost immediately (Walter et al., 1996, supra; Kay et al., 1994, Proc. Natl. Acad. Sci. USA 91:2353-2357). However, the immunological consequences of this approach are undesirable. In the case of AAV-hF.IX, the gradual rise in plasma hF.IX levels over a period of weeks indicates that patients preferably should continue the use of hF.IX concentrates for the initial period immediately surrounding intramuscular AAV vector treatment. This is not a barrier to treatment. The t1/2 of exogenously administered hF.IX is about 12 hours; thus plasma hF.IX levels may return to baseline before rising as a result of expression of the transgene. Further, expression of rAAV-introduced transgenes in muscle tissue persists for long periods if cross-species boundaries are not transgressed (Kessler et al., 1996, supra). For all of these reasons, administration of rAAV vectors expressing hF.IX to patients having hemophilia B is a feasible strategy for treatment of this disease.

In addition to the above, the observation that hF.IX co-localizes with collagen IV also has important implications for treatment of patients having hemophilia B. This finding is of interest not only as it relates to the staining pattern seen for F.IX, but also because it likely accounts for the previously reported findings of low efficiency of transfer of muscle cell-synthesized F.IX into the circulation. If collagen IV in the interstitial spaces serves as a high-affinity binding site for hF.IX, then this area may in effect function as a "sink" for hF.IX synthesized in muscle. Clearly, however, the trapping of hF.IX in the interstitial spaces by collagen IV is not an insurmountable obstacle to gene therapy, as the experiments in Rag 1 mice demonstrate. Moreover, as described herein, it is possible to generate an AAV hF.IX vector encoding hF.IX comprising a mutation which renders hF.IX capable of binding to collagen IV, thereby overcoming this potential drawback.

EXAMPLE 2

Studies in Dogs Having Hemophilia B

The experiments which are presented in this example are summarized as follows.

Dogs that have a point mutation in the catalytic domain of the F.IX gene, which, based on modeling studies, appears to render the protein unstable, suffer from severe hemophilia B (Evans et al., 1989, Proc. Natl. Acad. Sci. USA 86:10095-10099). Three such dogs were injected intramuscularly with AAV-cF.IX, containing the canine F.IX (cF.IX) gene. Administration of $8\times10^1$ AAV-cF.IX in dog B45 resulted in plasma levels of F.IX which were just at the threshold of detection (approximately 1-3 ng canine F.IX/ml of plasma). The whole blood clotting time (WBCT) was transiently shortened at various time points following vector administration. Beginning at 16 weeks after injection, sustained partial correction of the WBCT was observed; very low levels of plasma cF.IX have been observed to persist for at least 6 months. Immunofluorescence staining of sections obtained from biopsied muscle was performed and expression of cF.IX in the transduced muscle fibers was observed. No evidence for the production of antibodies specific for cF.IX was obtained when Western blotting analysis, ELISA or a coagulation inhibitor screen were performed. Intramuscular injection of $1\times10^{13}$ AAV-cF.IX into dog B46 resulted in plasma levels of cF.IX of up to approximately 17 ng of cF.IX/ml which was observed at 9 weeks post-injection. Partial correction of the WBCT was first observed at 2 weeks post-injection and was stable thereafter. The shortest WBCT in the absence of treatment with normal plasma (16 minutes) was measured at week 8. The improvements in the clotting time were corroborated by aPTT assay wherein decreases were evident at week 7 post-injection. Again, there was no evidence for the production of antibodies specific for cF.IX. Despite improvements in hemostatic parameters, the levels of cF.IX achieved to date are <1% of normal and not surprisingly, these treated dogs have experienced bleeding episodes. Increased doses of F.IX will be administered to dogs to achieve therapeutic benefit. In fact, dog B48 was recently injected intramuscularly with $7\times10^{13}$ AAV cF.IX and has yet to reach plateau levels. This dog developed a non-inhibitory antibody to cF.IX. The antibody was first detected at 14 days after injection and disappeared at 42 days after injection. Coincident with the disappearance of the antibody, the WBCT shortened into the range of 15-20 minutes where it has remained through the ensuing 45 days (i.e., a total of 90 days of observation). All of the dogs currently remain on study.

A. Intramuscular Administration of Canine F.IX in an AAV Vector

The Materials and Methods used in the experiments presented in this example are now described.

Figure 7:
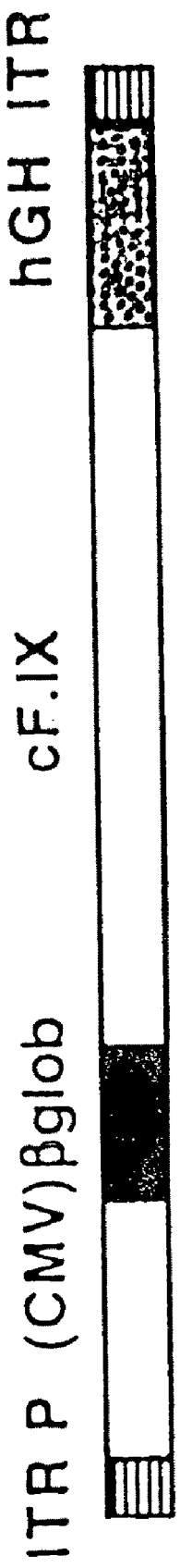
FIG. 7 is a diagram of AAV-cF.IX, i.e., canine F.IX in an AAV vector.

Viral Vector. AAV-cF.IX was generated as diagrammed in FIG. 7. The vector contains AAV inverted terminal repeats (ITR) flanking the following expression cassette: cytomegalovirus immediate early enhancer/promoter (P[CMV]), CMV splice donor/β-globin splice acceptor (βglob), cF.IX cDNA up to the EcoRI site at nucleotide position 2565, and human growth hormone polyadenylation signal (hGH).

Functional Integrity of cF.IX Transient transfection of 293 cells in the presence of vitamin K (6 μg/ml medium) was used to demonstrate that the cF.IX construct directed expression and secretion of functional cF.IX. The presence of cF.IX was assessed in media at 96 hours post-transfection and was also confirmed by a shortening of aPTT clotting time of F.IX-deficient human plasma after the addition of conditioned media. Different preparations of AAV-cF.IX were compared by infection of 293 cells with equal numbers of vector at various multiplicities of infection in the presence or absence of E1-deleted adenovirus. The amount of cF.IX produced was similar for the different preparations tested. 293 cells transduced with AAV-cF.IX at a multiplicity of infection of $4\times10^3$ in the absence of adenovirus produced 1.2 µg of cF.IX/ml medium/24 hours. Differentiated murine C2C12 myotubes in a 24 well plate transduced with $9\times10^9$ AAV-cF.IX per well produced 30-80 ng of cF.IX/ml medium/24 hours when assayed at 8-15 days post-infection.

Hemophilia B Dogs. A colony of dogs having severe hemophilia B comprising males that are hemizygous and females that are homozygous for a point mutation in the catalytic domain of the canine factor IX gene, has been maintained for more than two decades at the University of North Carolina, Chapel Hill (Evans et al., 1989, Blood 74:207-212). The hemostatic parameters of these dogs are well described and include the absence of plasma F.IX antigen, whole blood clotting times of >60 minutes, whereas normal dogs are 6-8 minutes, and prolonged activated partial thromboplastin time of 50-80 seconds, whereas normal dogs are 13-18 seconds. These dogs experience recurrent spontaneous hemorrhages. Typically, significant bleeding episodes are successfully managed by the single intravenous infusion of 10 ml/kg of normal canine plasma; occasionally, repeat infusions are required to control bleeding.

Intramuscular Injection. Under general anesthesia, male hemophilia B dogs (B45 and B46) and female hemophilia dog B48, all littermates, were injected percutaneously with AAV-cF.IX. The animals were not given normal canine plasma during the procedure.

and pre-treatment hemophilic dog plasma incubated with normal dog plasma). Neutralizing antibody titer against AAV vector was assessed.

Immunofluorescence Staining. Biopsied muscle obtained from dog B45 was placed in Optimal Cutting Temperature™ (OCT) (Tissue-TeK.®) OCT 4583 Compound, Sakura Finetek, Torrance, Calif.) in a cryovial, snap-frozen in liquid nitrogen-cooled 2-methyl butane for 7-10 seconds and then immediately transferred to liquid nitrogen and subsequently stored at –80° C. Cryosections of frozen muscle were stained as described herein using rabbit anti-cF.IX at a 1:100 dilution (Affinity Biologicals) as primary antibody and fluorescein isothiocyanate (FITC)-conjugated swine anti-rabbit IgG, diluted 1:30 (Dako Corp.) as secondary antibody. Cryosections were also used for hematoxylin and eosin (H&E) staining.

Vector Shedding. Swabs were taken and samples were resuspended in tissue culture medium. Swab samples were: lacrimal, nasal, rectal, saliva, and urine. A serum sample was also drawn. Samples were concentrated to a final volume of 200 µl using Centricon-100 vials, and DNA was extracted using the Qiamp blood kit (Qiagen). DNA was eluted in 200 µl TE, and 10 µl was used for PCR amplification using the AmpliTaq PCR kit (Perkin Elmer) in a final volume of 50 µl. PCR primers were as follows: upstream primer, 5'-ATA GCA GCT ACA ATC CAG CTA CCA TTC TGC-3' [SEQ ID NO:5] based on sequences in the cDNA of cF.IX, and downstream primer, 5'-TGG TAT CCC GTA GTA CAG GAA CAA ACC ACC-3' [SEQ ID NO:6] derived from sequences of the β-globin splice acceptor. The PCR product amplified by these primers was 698 bp. After 2 minutes of denaturation at 95° C., 40 cycles of 95° C./60° C./72° C. for 30 seconds/30 seconds/1

TABLE 1

| | Dog B45 | Dog B46 | Dog B48 |
|---|---|---|---|
| Date of birth | Apr. 21, 1997 | Apr. 21, 1997 | Apr. 21, 1997 |
| Date of administration | Jun. 20, 1997 | Aug. 18, 1997 | Dec. 5, 1997 |
| Weight at time of administration | 5.68 kg | 9.1 kg | 20 kg |
| Total AAV-cF.IX injected | Approximately $8 \times 10^{11}$ injected under guidance by ultrasound | Approximately $1 \times 10^{13}$ | Approximately $7 \times 10^{13}$ |
| Number of sites injected | 18 (5 sites in vastus lateralis, 4 sites in tibialis anterior, each hind limb) Some injections included carbon particles for subsequent visualization and biopsy of injection sites | 8 sites (2 sites in vastus lateralis, 2 sites in tibialis anterior, each hind limb) Some injections included carbon particles for subsequent visualization of injection sites | 60 sites |
| Vector concentration per injection site (approximate) | $5 \times 10^{10}$ in 250 µl | $1.3 \times 10^{12}$ in 375 µl | $1.2 \times 10^{12}$ in 300µ |

Analyses of Blood Samples. Whole blood clotting time (WBCT) was assessed as was ELISA for cF.IX in plasma. The ELISA is sensitive down to 3 ng/ml. Antibodies specific for cF.IX were assayed by ELISA and Western blotting. Activated partial thromboplastin time (aPTT) was measured. A coagulation inhibitor screen was also performed. Plasma obtained from a treated hemophilic dog and from a normal dog were mixed in equal volumes and was incubated for 2 hours at 37° C. The inhibitor screen was scored as positive if the aPTT clotting time was 3 seconds longer than that of the controls (normal dog plasma incubated with imidazole buffer minute, respectively, were performed, and were followed by incubation at 72° C. for 7 minutes. PCR products were visualized by agarose gel electrophoresis in the presence of ethidium bromide.

The Results of the experiments presented herein are now described.

Figure 8B:
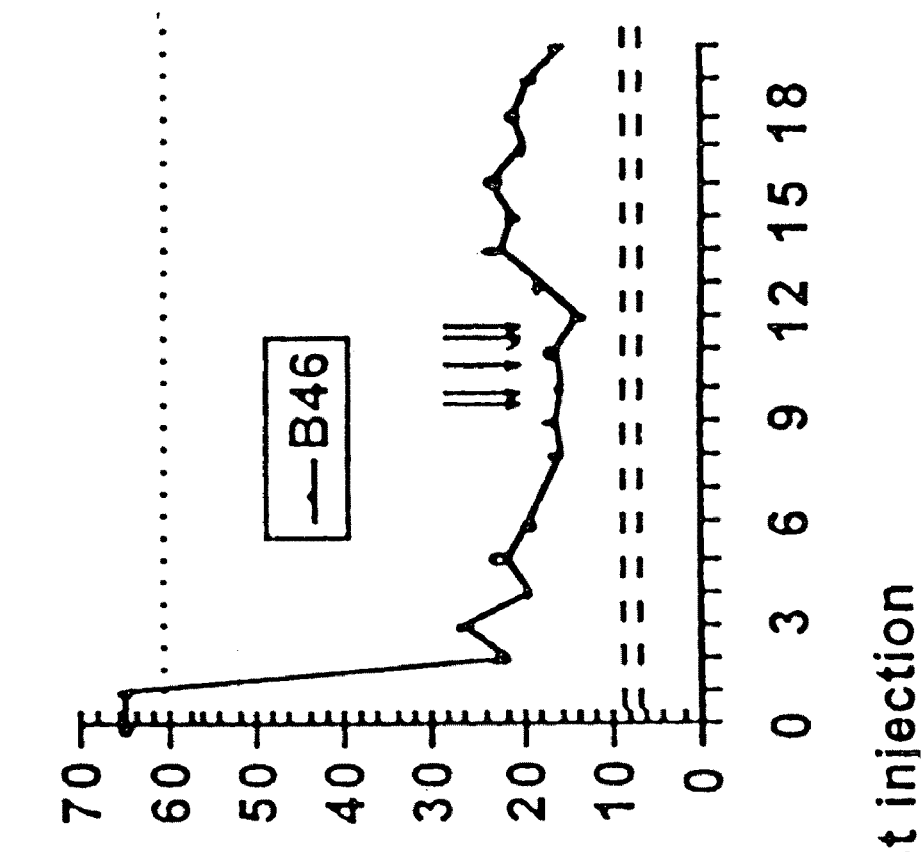
FIGS. 8A and 8B are a series of graphs depicting whole blood clotting time (WBCT) as a function of time after intramuscular injection of dog B45 with $8 \times 10^{11}$, and dog B46 with $1 \times 10^{13}$ AAV-cF.IX, respectively. If the blood sample did not completely clot within 60 min, the WBCT was indicated as 65 min. Asterisks (*) indicate partial clotting. WBCT of untreated hemophilia B dogs is >60 min (dotted line), and of normal dogs ranges from 6-8 min (broken line). Vertical arrows indicate treatment with normal plasma for bleeding episodes.
Figure 8A:
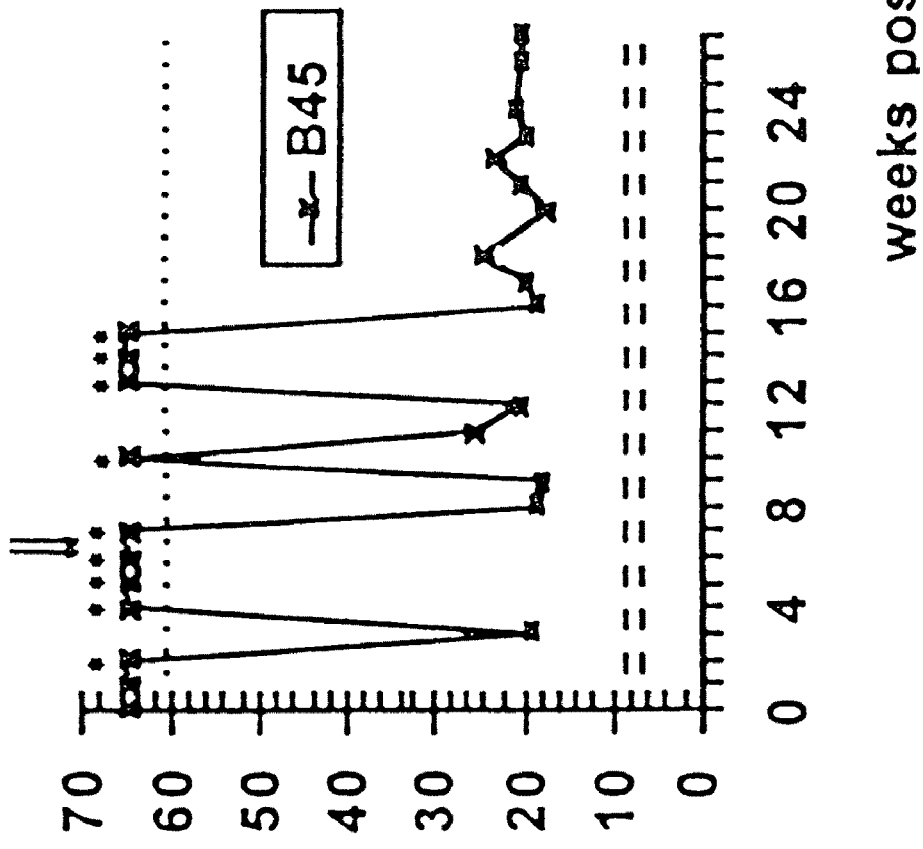
Figure 10B:
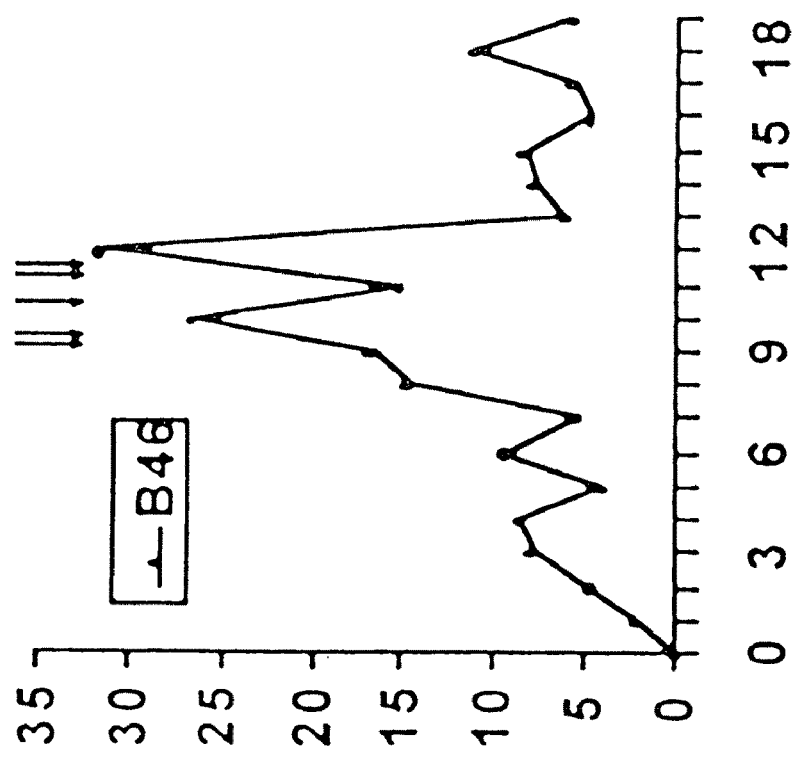
FIGS. 10A and 10B are a series of graphs depicting plasma levels of canine factor IX after intramuscular injection of hemophilia B dogs B45 and B46 with $8 \times 10^{11}$ or $1 \times 10^{13}$ AAV-cF.IX, respectively. Canine factor IX concentrations were measured by ELISA. Vertical arrows indicate treatment with normal plasma for bleeding. The elevated values in B46 from week 9 through week 12 are partially due to treatment with normal plasma.
Figure 10A:
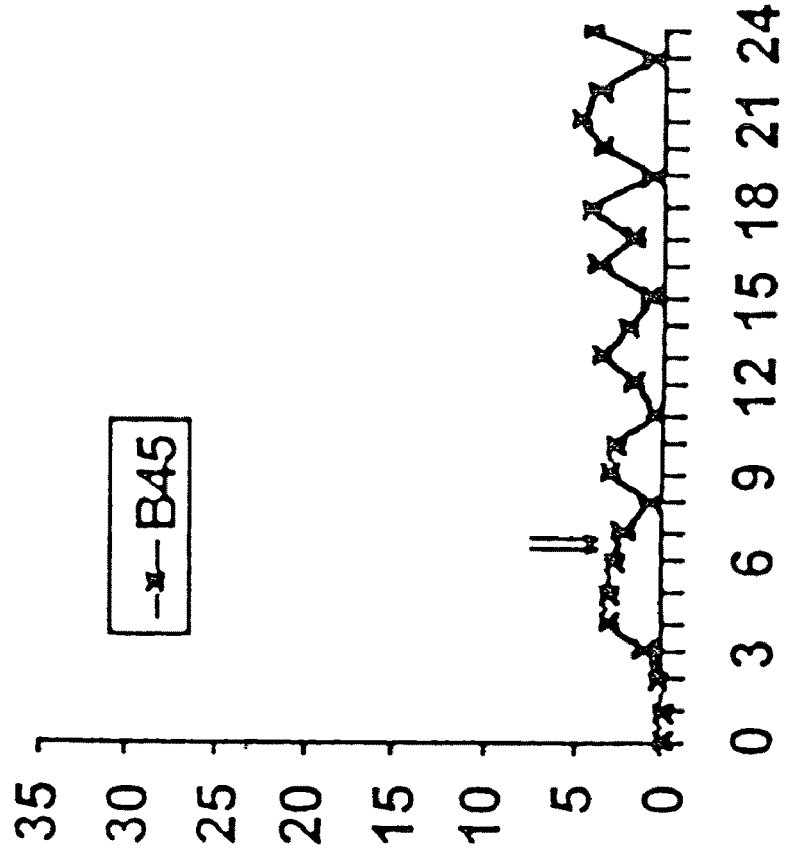
Figure 11:
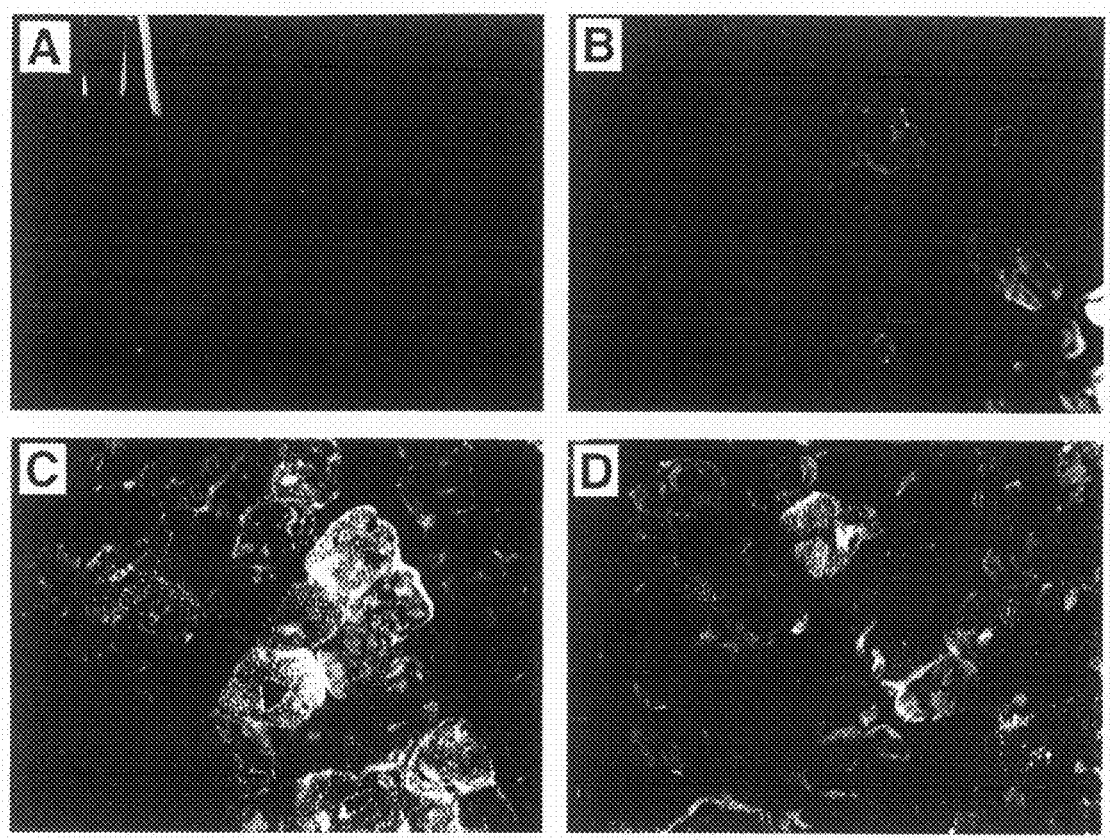
FIGS. 11A-11D are a series of images depicting immunofluorescence staining for cF.IX in skeletal muscle of dog B45.

Intramuscular (IM) injection of dog B45 with $8\times10^{11}$ AAV-cF.IX resulted in inconsistent effects upon hemostatic parameters. Whole blood clotting times (WBCT) were variable, ranging intermittently from approximately 20 minutes to >60 minutes (FIG. 8). Activated partial thromboplastin times (aPTT) were greater than 50 seconds, except for a single value at 3 weeks which was 48 seconds (FIG. 9). Levels of cF.IX as assessed by ELISA, were at the threshold of detection (1-3 ng/ml) beginning at 3 weeks post vector injection (FIG. 10). A muscle biopsy of an injection site was performed at 7 weeks after administration and confirmed intramuscular production of cF.IX by specific immunofluorescence staining (FIG. 11). Bleeding preceding the biopsy was successfully managed by treatment with normal canine plasma administered on days 46 and 47. Beginning at 16 weeks after injection, sustained partial correction of the WBCT was observed.

Following IM administration of a higher dose of AAV-cF.IX ($1 \times 10^{13}$), dog B46 exhibited significant improvement in hemostatic parameters that correlated with a sustained increase in plasma levels of cF.IX by ELISA. The WBCT was consistently lower than 20 minutes commencing at 2 weeks following vector administration and reached a nadir of 16 minutes at week 12 after vector injection (FIG. 8). Activated partial thromboplastin time (aPTT) decreased to 43 seconds by week 7 and then increased (FIG. 9). Plasma cF.IX antigen concentration assessed by ELISA increased over the first 9 weeks following injection to reach a level of approximately 17 ng/ml (FIG. 10). During week 10, this dog had an episode of bleeding into the right scapular region, which resolved after repeated infusions of normal canine plasma. The higher cF.IX values in the 3 week period following the hemorrhage are likely due to the plasma infusions (FIG. 10).

Dog B48 received the highest intramuscular dose of AAV-cF.IX ($7 \times 10^{13}$). This dog bled from an injection site following vector administration and received normal canine plasma at day 4. Data available at week 4 following injection (a timepoint not influenced by the plasma infusion), demonstrated a decreased WBCT (21.5 minutes) and canine factor IX level of 15 ng/ml. This dog is still on study and has not yet reached plateau levels. As noted herein, this dog transiently synthesized non-inhibitory antibody to cF.IX.

Dogs B45 and B46 had no measurable neutralizing antibodies specific for the AAV capsid prior to treatment. In each dog, high titers of anti-AAV capsid neutralizing antibodies ($10^3$-$10^4$) developed 7 days after vector administration and persisted throughout the test periods (through 17 weeks and 8 weeks for B45 and B46, respectively).

Analyses to detect antibodies specific for cF.IX, including Western blotting, ELISA assays and coagulation inhibitor screens, were negative at weeks 7, 13, 17, and 20 in dog B45. The higher dose dog, B46, had no detectable antibodies specific for cF.IX as measured by ELISA through week 9.

Virus shedding, as detected by PCR was positive at day 1 in serum, rectal, and saliva samples obtained from dog B45, and from day 1 serum of dog B46. All other samples obtained pre-treatment and >1 day after injection were negative.

TABLE 2

Results obtained from dogs receiving intramuscular injections

|  | Dog B45 | Dog B46 |
|---|---|---|
| Bleeding history | Bleeding following muscle biopsy was treated with normal plasma on days 46 and 47. Suring the window of plasma coverage given for the bleed, a muscle biopsy was obtained. | Shoulder bleed treated with normal plasma on days 67, 68, 72, 79, and 80. |
| WBCT (FIG. 8) | At week 2, partial clotting by 15-20 min. after the start of the assay, but complete clotting not observed. Subsequent WBCTs inconsistent, with partial corrections (18.5 to 28.5 min) at 8 timepoints and incomplete clot formation at 8 other points. Shortened WBCT at 2 of 8 times (weeks 8 and 9) partially due to treatment with normal plasma following muscle biopsy and bleeding (days 46 and 47) | >60 min during first week, consistently shortened after week 2. Shortest time in absence of treatment with normal plasma was 16 min at week 8. |
| aPTT+ (FIG. 9) | 48 seconds at week 3. All other values were above 50 seconds. | Partial correction (43 seconds) was first observed at week 7. |
| Canine Factor IX antigen levels by ELISA (FIG. 10) | Detectable at week 3. Subsequent antigen levels varied between 1-4 ng/mL. | Detectable at low levels starting at 1 week and increased to 17 ng/ml plasma at week 9 |
| Antibody screens | Tested by Western blot, ELISA and coagulation inhibitor screen through week 30. No evidence for antibodies against canine factor IX was found. | None detectable by ELISA measured through week 26 |
| Neutralizing antibody to AAV capsid | None detectable prior to treatment. Titer of $10^3$ to $10^4$ detected at week 1 post-injection and persisting for at least 17 weeks | None detectable prior to treatment. High titer ($10^4$) detected at week 1 and persisting for at least 8 weeks. |
| Immunofluorescence staining (FIG. 11) | Canine factor IX production seen in tibialis anteriot muscle fibers biopsied on week 7†. | To be done |

TABLE 2-continued

Results obtained from dogs receiving intramuscular injections

| | Dog B45 | Dog B46 |
|---|---|---|
| | Protein lysates of muscle sample were tested by ELISA and showed up to 1.8 ng canine factor IX/mg tissue and up to 25 ug canine factor IX/mg protein. | |
| Viral shedding | AAV-cF.IX sequences were detected in serum at day 1 (strong signal) and rectal and saliva samples at day 1 (weak signals). No signals obtained on pre-treatment samples and on samples from day 4 and weeks 1, 2, 3, and 5. | Positive PCR signal from day 1 serum sample. Samples taken pre-injection and at day 4 and at weeks 1 and 2 were negative. |

Bleeding resolved following treatment with normal canine plasma.
*Normal dogs: 13.5-17 seconds. Untreated hemophilic dogs: 50-80 seconds.
†Carbon particles co-injected with AAV vector were found on H&E-stained; slides of serial sections.

The data presented in this example demonstrate that dogs having hemophilia B can synthesize sustained plasma levels of cF.IX following a single intramuscular administration of AAV-cF.IX. The long-term (>4 months) systemic cF.IX levels were associated with modest improvements in hemostatic parameters. However, the treated dogs experienced spontaneous bleeds indicating that these levels were sub-therapeutic. The prolonged time-course to plateau levels in dog B46 and the suggestion of a dose-response in these dogs demonstrates a similarity between the canine and murine models. The F.IX that is secreted by the transduced canine muscle is biologically active, based upon shortening of WBCT and aPTT. In summary, intramuscular administration of AAV-cF.IX in these dogs with hemophilia B was well tolerated.

B. Portal Vein Administration of cF.IX in an AAV Vector

The Materials and Methods used in the experiments presented in this example are now described.

Viral Vector. AAV-EF1α-cF.IX was generated using ordinary molecular biology technology. The vector contains a 2.5 kb fragment of the human elongation factor 1α. gene (EF1α), which includes the enhancer, promoter, first exon and first intron, and a portion of the non-coding region of exon 2. The EF1α promoter was chosen because vectors containing it exhibit increased transgene expression following portal vein administration. This region of EF1α is positioned upstream of the cF.IX cDNA (up to the EcoRI site at nt 1731) and the human growth hormone polyadenylation signal (hGH). The entire expression cassette is flanked by AAV inverted terminal repeats (ITR). The functional integrity of this vector was demonstrated by ELISA analysis of F.IX produced in 293 cells.

Portal Vein Administration. The abdomen of hemophilic dog B44 was aseptically and surgically opened under general anesthesia and a single infusion of $3 \times 10^{12}$ AAV-EF1α-cF.IX was administered into the portal vein. This animal was protected from hemorrhage in the peri-operative period by intravenous administration of normal canine plasma. The dog was sedated, intubated to induce general anesthesia, and the abdomen was shaved and prepped. After the abdomen was opened, the spleen was moved into the operative field. The splenic vein was located and a suture was loosely placed proximal to a small distal incision in the vein. An introducer was rapidly inserted into the vein, then the suture loosened, and a 5 F cannula was threaded to an intravenous location near the portal vein bifurcation. After hemostasis was secured and the catheter balloon was inflated, approximately 5.0 ml of vector diluted in PBS was infused into the portal vein over a 5 minute interval. The vector infusion was followed by a 5.0 ml infusion of saline. The balloon was then deflated, the cannula was removed and venous hemostasis was secured. The spleen was then replaced, bleeding vessels were cauterized and the operative wound was closed. The animal was extubated having tolerated the surgical procedure well.

Blood samples were analyzed as described herein for intramuscular injections.

The Results of the experiments presented herein are now described. No evidence of circulating F.IX was detected by ELISA and no effect on hemostatic parameters was apparent through 4 months post-injection of the animal. No clinical signs of acute or chronic toxicity were apparent following administration of the vector to the animal, indicating that intravascular injection of this vector is well tolerated, and apparently non-toxic. No inhibitors were detected.

EXAMPLE 3

Absence of Inhibitors in Mice Following Intramuscular Injection of AAV-mF.IX

The administration of AAV-hF.IX intramuscularly to a mammal is accompanied by the potential risk of the development of inhibitors to F.IX in the mammal. The normal site of F.IX synthesis is the liver. A valid concern for any approach based on expression in an ectopic site is whether biosynthesis will result in some change in the protein that will render it nonfunctional or immunogenic, for example, through alterations in post-translational processing. To test this possibility, AAV-mouse F.IX (mF.IX) was administered to the muscle of three strains of immunocompetent mice, and the mice were assessed to determine whether antibodies to the autologous transgene product were generated. Two methods were used to demonstrate that anti-mF.IX antibodies (i.e., inhibitors) did not develop in the mice. The presence of antibodies to AAV-mF.IX was assessed by Western blotting. Anti-AAV-mF.IX antibodies were not detected using this method. A coagulation inhibitor screen was also used to assess whether inhibitors were synthesized in the mice and again, this test established that inhibitors were not synthesized in these animals. The synthesis of mF.IX in mouse muscle resulted in the production of a protein which was viewed by the immune system as being a self protein. Thus, the use of this approach, i.e., the delivery of F.IX to muscle tissue using an AAV vector is a clinically viable method for treatment of hemophilia.

The Materials and Methods used in the experiments presented in this example are now described.

Figure 12:
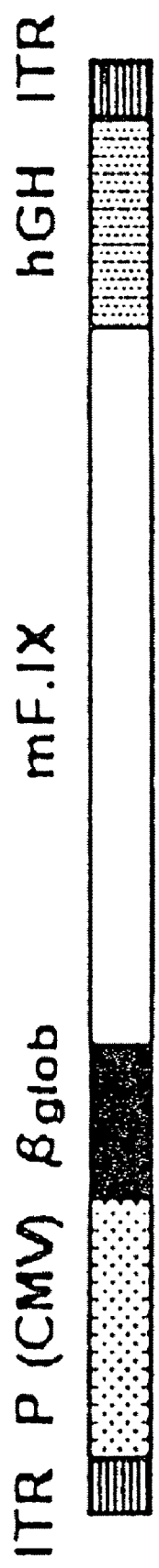
FIG. 12 is a diagram of AAV-mF.IX, i.e., mouse F.IX in an AAV vector.

Viral Vectors. AAV-MF.IX (FIG. 12) contained two AAV inverted terminal repeats (ITR) flanking the following expression cassette: the cytomegalovirus immediate early enhancer/promoter (P[CMV]), CMV splice donor/β-globin splice acceptor (βglob), the 2.7 kb murine factor IX cDNA, and the human growth hormone polyadenylation signal (hGH). The mF.IX cDNA (Wu et al., 1990, Gene 86:275-278) contained a number of errors that had been introduced by PCR. Site-directed mutagenesis was used to restore the wild-type sequence, which was confirmed by DNA sequencing. The functional integrity of mF.IX encoded by the vector was tested by transducing the 293 cell line 84-31 and evaluating the vitamin K-containing conditioned media using an aPTT assay. The addition of supernatants obtained from transduced cells to mF.IX deficient plasma, resulted in a shortening of the clotting time. This was not the case when supernatants obtained from control cells were used.

Animal Procedures. Immunocompetent 5 month old female CD-1 mice, 5 month old female C57BL/6 mice (Charles River Breeding Laboratories, Wilmington, Mass.) and 5 week old male BALB/c mice (The Jackson Laboratory) (n=3 for each strain) were used in this study. The quadriceps and tibialis anterior muscles of both hind limbs of the mice were injected with a total dose of $1 \times 10^{11}$ AAV-mF.IX as described herein. Litter mates were injected by the same method with $2 \times 10^{10}$ AAV-hF.IX. Retro-orbital bleeding was used to collect plasma samples as described (Walter et al., 1996, Proc. Natl. Acad. Sci. USA 93:3056-3061).

Detection of Murine Antibodies by Western Blot Analysis of Plasma Samples. Western blots were performed by separating 100 ng of hF.IX (Mononine** plasma-derived factor IX, Armour) or mF.IX (purified from tissue culture media obtained from stably transfected 293 cells) on SDS-PAGE gels followed by transfer of the proteins onto Hybond-ECL membrane (Amersham). Blocking was accomplished using BLOTTO (5% non-fat dry milk, 10 mM Tris-HCl, pH 8.0, 2 mM $CaCl_2$, 0.05% Tween-20) for 2 hours. The plasma samples which were diluted 1:200 in BLOTTO, were incubated for 1 hour with the membranes. Horseradish peroxidase conjugated goat anti-mouse IgG diluted 1:1000 in BLOTTO (Boehringer Mannheim) served as the secondary antibody. Anti-factor IX was visualized by ECL detection and film development (Amersham). The positive control plasma for this Western blot was obtained from a hemophilia B mouse which developed antibodies against both mF.IX and hF.IX following intravenous injection of an adenoviral vector containing the gene for human factor IX (Kung et al., 1998, Blood 91:784-790).

aPTT Assay. Mouse plasma was collected in citrate buffer during bleeding from the tail vein. Clotting times in the aPTT assay were conducted by mixing 50 μl of aPTT reagent (Organon Teknika, Durham, N.C.) with 50 μl of murine plasma. The mixture was incubated at 37° C. for 3 minutes, and 50 μl of 25 mM $CaCl_2$ was added. The clotting time was measured using a fibrometer (BBL FibroSystem).

Coagulation Inhibitor Screen. Plasma obtained from a vector injected mouse was mixed with an equal volume of normal pooled murine plasma and was incubated for 2 hours at 37° C. An aliquot was withdrawn and was mixed with aPTT reagent. The inhibitor screen was scored as positive if the aPTT clotting time was 3 seconds longer than that of the control (normal plasma incubated with imidazole buffer).

The Results of the experiments presented in this example are now described.

Figure 13:
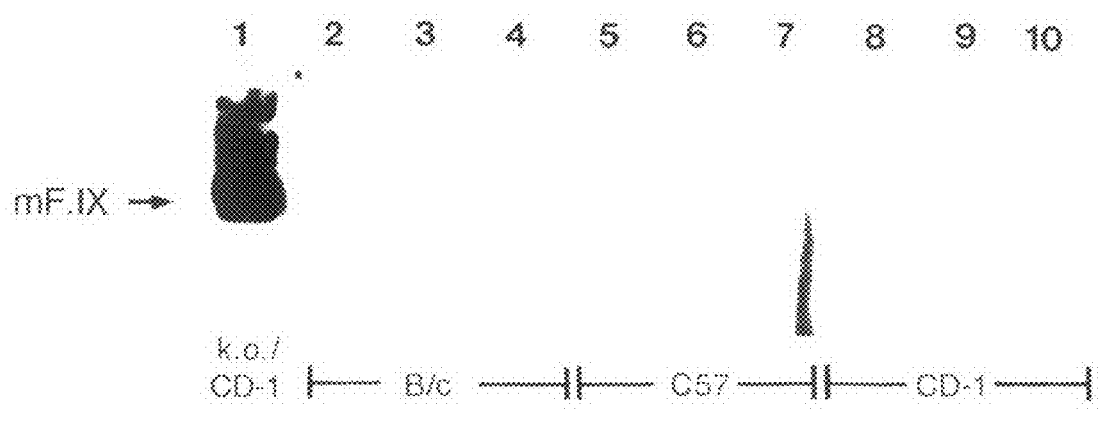
FIG. 13 is an image of a Western Blot for detection of antibodies in mouse plasma specific for mF.IX. mF.IX was transferred onto a nitrocellulose membrane and was incubated in the presence of various mouse plasma samples followed by incubation with horseradish peroxidase conjugate anti-mouse IgG and ECL detection. Lane 1—Plasma obtained from hemophilia B mouse bred on CD-1 background that had developed antibodies specific for hF.IX after intravenous injection of Ad-hF.IX. These antibodies cross-reacted with murine factor IX. Lanes 2-10—Plasma obtained from mice injected intramuscularly with AAV-mF.IX. Lanes 2-4—BALB/c mice. Lanes 5-7—C57BL/6 mice. Lanes 8-10—CD-1 mice. All samples were obtained from mice at day 60 post-injection.

None of the mice injected with AAV-mF.IX developed antibody specific for mF.IX when assayed by Western blotting at 18 days and 60 days post-injection (FIG. 13, lanes 2-10). Clotting times by aPTT on plasma samples of all vector injected mice were within the normal range (approximately 25 seconds) when measured at 60 days post-injection. Inhibitor assays on all the injected mice also demonstrated the absence of inhibitors. The control mice injected with AAV-hF.IX all developed antibodies specific for hF.IX within the first 2 weeks of injection, demonstrating the immunocompetence of these animals.

These data confirm that mice which were injected with AAV-F.IX did not synthesize inhibitors directed against F.IX.

EXAMPLE 4

Biochemical Analysis of Human Factor IX Produced by Skeletal Muscle

The natural site of F.IX synthesis is within hepatocytes. The experimental approach described herein targets the myotubes of skeletal muscle as the site of F.IX production. Human F.IX is purified from conditioned medium of human myotubes that are maintained in tissue culture following transfection of the cells with AAV-CMV-hF.IX. Preliminary studies performed to date demonstrate that the myotube-synthesized F.IX is correctly processed in these cells at the N-terminus, and is γ-carboxylated. In addition, the conditioned medium corrects the aPTT when added to human F.IX deficient plasma.

EXAMPLE 5

Clinical Protocol Summary for Administration of AAV-hF.IX to Humans

A generation of clinical research in patients treated with clotting factor concentrate has documented that minimal elevations in the levels of circulating clotting factor are sufficient to prevent much of the morbidity and mortality of the disease. The most comprehensive data are contained in the Swedish prophylaxis studies (Lofqvist et al., 1997, J. Int. Med. 241:395-400) wherein, since 1958, most hemophilia patients in Sweden have been maintained on a regimen in which clotting factor is infused on a regular basis rather than in response to bleeds. The goal of gene therapy is to maintain consistent levels of F.IX which are greater than 1% of normal. The gene therapy described herein as a treatment for patients having severe hemophilia, particularly, hemophilia B, thus affords the well documented benefits of maintaining constant, yet therapeutic levels of F.IX in the blood stream of patients.

In a Phase I clinical study, it is proposed that the initial trial is limited to patients having severe disease (i.e., having less than 1% of normal circulating levels of F.IX), who have no history of the development of inhibitors and whose life expectancy is shortened by the disease.

During the study, the safety of inter-patient dose escalations of AAV-F.IX administered intramuscularly will be monitored. Toxicity related to the delivery of the vector locally and systemically will be evaluated. By following the protocols described herein, the potential efficacy of each dose group will be monitored by measuring biological and physiological activity of the transgene product. Analyses will be performed to detect the presence of the F.IX gene and protein expression at the site of injection.

In the initial study, at least twelve patients will be included. These patients will be assigned to groups of three patients each, and each patient within each group will receive the same dose of AAV-hF.IX. The first group of patients will receive a total dose based upon results from a study to determine toxicity in rats. The rat toxicity study is performed according to accepted animal toxicity study protocols, prior to the initiation of the Phase I clinical trial (Food and Drug Administration Good Laboratory Practices as found in the 21 C.F.R. §58). The starting dose in patients will be at least 10-fold lower, on a per kilogram basis, than the lowest dose resulting in unacceptable toxicity following administration to rats. If no toxicity is observed at the highest dose administered to rats, the starting dose in human patients will be at least 10-fold lower than this highest dose. If no dose limiting toxicity and no evidence of gene expression is observed in the first group of patients and at least eight weeks has elapsed since the last patient was treated, a second group of patients will be treated at a dose of one log higher than the initial Group 1 patient dose. If no dose limiting toxicity or expression is observed, this schedule will be repeated until expression is observed in the absence of dose limiting toxicity. Thereafter, doses will be escalated by half log increments until there is evidence of biological and physiological efficacy in the absence of unacceptable toxicity.

Within the two hours preceding vector administration, patients will be infused with a dose of highly purified coagulation F.IX concentrate calculated to raise the F.IX level in the patient to 100%. Intramuscular injections will be carried out under anesthesia in the form of conscious sedation according to hospital protocol. A volume of 0.5 ml will be administered in each injection site; the vector concentration and number of injection sites will vary in relation to dose. In the low dose groups, approximately six sites will be injected, and in the highest dose group, approximately twenty sites will be injected. Patients will be hospitalized for two to three days. Studies in dogs indicate no shedding of vector beyond 24 hours following injection. Nonetheless, standard reverse isolation procedures will be followed during hospitalization.

In follow-up treatment, patients will receive F.IX concentrate to achieve levels of 50% of normal at approximately twelve hours after injection of vector, and every twenty four hours thereafter for three to seven days depending upon clinical evaluation.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A pharmaceutical composition comprising a virus, said virus comprising a recombinant adeno-associated virus vector comprising at least two adeno-associated virus inverted terminal repeats, a promoter/regulatory sequence, isolated DNA encoding Factor IX and accompanying 5' and 3' untranslated regions and a transcription termination sequence, wherein said isolated DNA encoding Factor IX comprises a mutation encoding an alanine residue in place of lysine in the fifth amino acid position from the beginning of mature Factor IX.

2. The composition of claim 1, further comprising a portion of intron 1 of the Factor IX gene.

3. The composition of claim 2, wherein said portion of intron 1 of a Factor IX gene is from about 0.3 kb to about 1.7 kb.

4. The composition of claim 1 further comprising a pharmaceutically acceptable carrier.

5. The composition of claim 1, wherein said promoter/regulatory sequence comprises the cytomegalovirus immediate early promoter/enhancer.

6. The composition of claim 1, wherein said transcription termination signal is the SV40 transcription termination signal.

7. A kit comprising the pharmaceutical composition of claim 1.

8. The composition of claim 1 wherein said Factor IX is human Factor IX.

* * * * *